United States Patent [19]
Taylor et al.

[11] Patent Number: 5,449,344
[45] Date of Patent: * Sep. 12, 1995

[54] SYRINGE APPARATUS WITH PRESSURE GAUGE AND DETACHABLE TIMER

[75] Inventors: Steven R. Taylor; Fred P. Lampropoulos, both of Salt Lake City; Thomas D. Stout, Sandy; A. Tony Smith, Salt Lake City, all of Utah

[73] Assignee: Merit Medical Systems, Inc., South Jordan, Utah

[ * ] Notice: The portion of the term of this patent subsequent to Nov. 9, 2010 has been disclaimed.

[21] Appl. No.: 148,464

[22] Filed: Nov. 5, 1993

Related U.S. Application Data

[63] Continuation-in-part of Ser. No. 900,987, Jun. 18, 1992, Pat. No. 5,259,838.

[51] Int. Cl.$^6$ .............................................. A61M 29/00
[52] U.S. Cl. ............................... 604/97; 604/96; 604/99; 604/100; 604/207; 606/192
[58] Field of Search ........................... 604/96–100, 604/207, 208–211, 224; 606/192

[56] References Cited

U.S. PATENT DOCUMENTS

| | | | |
|---|---|---|---|
| 383,940 | 6/1888 | Brinkerhoff | |
| 404,105 | 5/1889 | Overlach | |
| 446,125 | 2/1891 | Schirmer | |
| 577,682 | 2/1897 | Eissner | |
| 730,054 | 6/1903 | Sheets | |
| 1,661,818 | 3/1928 | Cook | |
| 1,707,880 | 4/1929 | Sheets | |
| 2,656,836 | 10/1953 | Hickey | 128/218 |
| 2,672,866 | 3/1954 | Kater | 128/218 |
| 2,699,168 | 1/1955 | Lewis | 128/218 |
| 2,724,385 | 11/1955 | Lockhart | 128/261 |
| 2,736,315 | 2/1956 | Feeney | 128/218 |
| 2,764,978 | 10/1956 | Everett | 128/215 |
| 3,080,866 | 3/1963 | Friedman | 128/218 |
| 3,388,941 | 6/1968 | Marcus | 294/4 |
| 3,478,937 | 11/1969 | Solowey | 222/386 |
| 3,491,757 | 1/1970 | Arce | 128/221 |

(List continued on next page.)

FOREIGN PATENT DOCUMENTS

| | | |
|---|---|---|
| 545415 | 8/1957 | Canada . |
| 0119296 | 9/1984 | European Pat. Off. . |
| 0230966A3 | 1/1985 | European Pat. Off. . |

(List continued on next page.)

OTHER PUBLICATIONS

Reference Catalog of Schneider Shiley for disposable and reusable inflation devices, including a reusable manometer gauge (1987).

Peripheral Product Catalog of Schneider for disposable and reusable inflation devices, including a reusable manometer gauge (1990).

Peripheral Division Product Catalog of Schneider an-
(List continued on next page.)

Primary Examiner—C. Fred Rosenbaum
Assistant Examiner—Bryan L. Tsosie
Attorney, Agent, or Firm—Workman Nydegger & Seeley

[57] ABSTRACT

A syringe apparatus for use with balloon-tipped catheters is disclosed having a pressure gauge and timer assembly. In one mode, the timer assembly displays the duration of a current event of inflation or deflation, and the duration of the most recent past event of inflation or deflation. In another mode, the timer assembly displays historical information showing the event number and duration of past events of inflation and deflation. The pressure gauge display and the timer assembly display are situated conveniently on the syringe assembly and in proximity to one another so as to enable a syringe operator to substantially simultaneously monitor durations of inflation and deflation without the need for an assistant, yet without requiring purchase or use of computerized monitors. In another mode, the timer assembly can be detached from the syringe assembly at the completion of an inflation procedure and then reused with another syringe assembly. In this mode, the pressure gauge is permanently mounted to the syringe assembly, or alternatively, it is mounted to the detachable timer assembly so as to also be reusable.

17 Claims, 16 Drawing Sheets

U.S. PATENT DOCUMENTS

| | | | |
|---|---|---|---|
| 3,529,596 | 9/1970 | Garner | 128/145.6 |
| 3,698,381 | 10/1972 | Federico et al. | 128/1 R |
| 3,720,199 | 3/1973 | Rishton et al. | 128/1 D |
| 3,884,229 | 5/1975 | Raines et al. | 128/221 |
| 3,931,822 | 1/1976 | Marici | 128/351 |
| 3,966,358 | 6/1976 | Heimes et al. | 417/12 |
| 3,985,123 | 10/1976 | Herzlinger et al. | 128/2.05 F |
| 3,992,926 | 11/1976 | Berryhill | 73/80 |
| 4,016,871 | 4/1977 | Schiff | 128/2.06 R |
| 4,057,050 | 11/1977 | Sarstedt | 128/2 F |
| 4,063,662 | 12/1977 | Drummond et al. | 222/31 |
| 4,086,653 | 4/1978 | Gernes | 364/564 |
| 4,106,002 | 8/1978 | Hogue, Jr. | 340/626 |
| 4,182,344 | 1/1980 | Benson | 128/207.15 |
| 4,254,773 | 3/1981 | Waldbillig | 128/348 |
| 4,261,360 | 4/1981 | Perez | 128/230 |
| 4,266,550 | 5/1981 | Bruner | 128/349 |
| 4,267,846 | 5/1981 | Kontos | 128/765 |
| 4,285,340 | 8/1981 | Gezari et al. | 128/205.24 |
| 4,323,071 | 4/1982 | Simpson et al. | 128/343 |
| 4,332,254 | 6/1982 | Lundquist | 128/344 |
| 4,370,982 | 2/1983 | Reilly | 604/98 |
| 4,384,470 | 5/1983 | Fiore | 73/4 R |
| 4,404,974 | 9/1983 | Titus | 128/670 |
| 4,418,392 | 11/1983 | Hata | 364/571 |
| 4,439,185 | 3/1984 | Lundquist | 604/97 |
| 4,444,335 | 4/1984 | Wood et al. | 222/43 |
| 4,446,715 | 5/1984 | Bailey | 73/1 R |
| 4,446,867 | 5/1984 | Leveen et al. | 128/344 |
| 4,466,426 | 8/1984 | Blackman | 128/1.1 |
| 4,504,268 | 3/1985 | Herlitze | 604/170 |
| 4,522,194 | 6/1985 | Normann | 128/1 D |
| 4,526,196 | 7/1985 | Pistillo | 137/557 |
| 4,546,760 | 10/1985 | Suzuki et al. | 128/1 D |
| 4,557,269 | 12/1985 | Reynolds et al. | 128/675 |
| 4,568,335 | 2/1986 | Updike et al. | 604/211 |
| 4,573,978 | 3/1986 | Reilly | 604/240 |
| 4,583,917 | 4/1986 | Shah | 417/63 |
| 4,583,974 | 4/1986 | Kokernak | 604/211 |
| 4,585,010 | 4/1986 | Ascer et al. | 128/673 |
| 4,596,255 | 6/1986 | Snell et al. | 128/697 |
| 4,597,381 | 7/1986 | Oumi et al. | 128/6 |
| 4,600,015 | 7/1986 | Evans et al. | 128/780 |
| 4,601,701 | 7/1986 | Mueller, Jr. | 604/83 |
| 4,610,256 | 9/1986 | Wallace | 128/675 |
| 4,621,646 | 11/1986 | Bryant | 128/692 |
| 4,651,738 | 3/1987 | Demer et al. | 128/344 |
| 4,655,749 | 4/1987 | Fischione | 604/98 |
| 4,658,829 | 4/1987 | Wallace | 128/672 |
| 4,672,974 | 6/1987 | Lee | 128/673 |
| 4,706,670 | 11/1987 | Andersen et al. | 128/344 |
| 4,710,179 | 12/1987 | Haber | 604/211 |

(List continued on next page.)

FOREIGN PATENT DOCUMENTS

| | | |
|---|---|---|
| 0149866 | 7/1985 | European Pat. Off. . |
| 0446932A2 | 3/1990 | European Pat. Off. . |
| 0396353 | 7/1990 | European Pat. Off. . |

(List continued on next page.)

OTHER PUBLICATIONS nouncing disposable and reusable inflation devices, including a reusable manometer gauge. (1990).

Advertisement brochure of ACS entitled: "When Complex Anatomy Demands a Simplified Approach." (1988).

Product catalog of Mansfield (1988).

Advertisement brochure of Mansfield entitled "The Mansfield Trak Series" (1987).

Advertisement brochure of Mansfield entitled: "The Mansfield Series 3000 Intra-Aortic Balloon Pump".

Product brochure of Mansfield for the Max Trak D.P. inflation device.

Brochure of SciMed Life Systems, Inc. of the SciMed Inflation Device having a lighted analog gauge.

Brochure of ACS for the New Indeflator Plus 20. (1988).

Product brochure of Medex, Inc. for the Medflator. (1991).

Brochure for SciMed Life Systems, Inc. entitled "The New 7F Triguide Guiding Catheter" (1991).

Advertisement brochure of SciMed Life Systems, Inc. entitled: "Good News for People with Only Two Hands." (1988).

Advertisement brochure of Baxter Healthcare Corp. for Inflation Pro. (1986).

Advertisement brochure of C. R. Bard, Inc. USCI Division of USCI Wizard Disposable Inflation Device (1987).

Advertisement brochure of Medex, Inc. for Medflator inflation system (1991).

Advertisement brochure of Mansfield for Digiflator inflation syringe with an attached digital pressure gauge.

(List continued on next page.)

U.S. PATENT DOCUMENTS

| | | | |
|---|---|---|---|
| 4,715,854 | 12/1987 | Vaillancourt | 604/191 |
| 4,723,556 | 2/1988 | Sussman | 128/748 |
| 4,723,938 | 2/1988 | Goodin et al. | 604/99 |
| 4,743,230 | 5/1988 | Nordquest | 604/97 |
| 4,758,223 | 7/1988 | Rydell | 604/90 |
| 4,781,192 | 11/1988 | Demer | 128/344 |
| 4,787,368 | 11/1988 | Kageyama | 600/18 |
| 4,787,429 | 11/1988 | Valentini et al. | 141/383 |
| 4,796,606 | 1/1989 | Mushika | 600/18 |
| 4,799,491 | 1/1989 | Eckerle | 128/672 |
| 4,817,629 | 4/1989 | Davis | 128/748 |
| 4,819,637 | 4/1989 | Dormandy, Jr. et al. | 128/325 |
| 4,820,271 | 4/1989 | Deutsch | 604/99 |
| 4,825,876 | 5/1989 | Beard | 128/675 |
| 4,830,013 | 5/1989 | Maxwell | 128/637 |
| 4,832,692 | 5/1989 | Box et al. | 604/99 |
| 4,838,864 | 6/1989 | Peterson | 604/100 |
| 4,858,615 | 8/1989 | Meinema | 128/668 |
| 4,872,483 | 10/1989 | Shah | 137/557 |
| 4,877,035 | 10/1989 | Bogen et al. | 128/673 |
| 4,896,671 | 1/1990 | Cunningham et al. | 128/642 |
| 4,901,731 | 2/1990 | Millar | 128/675 |
| 4,906,244 | 3/1990 | Pinchuk et al. | 606/194 |
| 4,907,596 | 3/1990 | Schmid et al. | 128/672 |
| 4,919,121 | 4/1990 | Rydell et al. | 604/97 |
| 4,940,459 | 7/1990 | Noce | 604/97 |
| 4,974,774 | 12/1990 | Nakagawa et al. | 600/18 |
| 5,004,472 | 4/1991 | Wallace | 606/194 |
| 5,009,662 | 4/1991 | Wallace et al. | 604/100 |
| 5,019,041 | 5/1991 | Robinson et al. | 604/97 |
| 5,021,046 | 6/1991 | Wallace | 606/97 |
| 5,085,060 | 1/1992 | Freund et al. | 606/192 |
| 5,086,777 | 2/1992 | Hishii | 128/675 |
| 5,135,488 | 8/1992 | Foote et al. | 604/100 |
| 5,279,563 | 1/1994 | Brucker et al. | 604/98 |

FOREIGN PATENT DOCUMENTS

| | | |
|---|---|---|
| 2083364A | 3/1982 | United Kingdom . |
| WO81/02664 | 10/1981 | WIPO . |
| WO92/17221 | 10/1992 | WIPO . |

OTHER PUBLICATIONS

Mansfield instruction brochure for the Digiflator. (1991).

Product catalog of ACS (1991).

Product catalog of C. R. Bard, Inc. USCI Division (1988).

"ACS Accessories Offer Optimum Efficiency in Your Angioplasty Procedures," Eli Lilly and Company—published before the filing date of applicants' patent application.

Advertising brochure of North American Instrument Corporation entitled "The NAMIC 10cc Angiographic Syringe Features."—published before the filing date of applicants' patent application.

Advertising brochure of Spetramed, Inc.; product brochure for "Controlease Disposable Control Syringe"; and product brochure for control syringe of COEUR Laboratories, Inc.—published before the filing date of applicants' patent application.

"Clearing the Path for a Healthy Heart," *Tristate: The Cincinnati Enquirier Magazine,* Oct. 23, 1988.

"Coronary Angioplasty," Krames Communications, 1985.

"Good News for People with Only Two Hands," SciMed Life Systems, Inc.—published before the filing date of applicants' patent application.

"Health—Critics of Angioplasty Worry About Inflated Success Claims," *U.S. News & World Report,* Jul. 25, 1988, p. 65.

"Inflation PRO: A New Dual-Support System for Angioplasty," Baxter Healthcare Corporation—published before the filing date of applicants' patent application.

"PTCA Safe and Efficacious Performed Together With Diagnostic Angiography in Selected Cases," *Cardiovascular News,* May 1988, p. 8.

"USCI Wizard Disposable Inflation Device," C. R. Bard, Inc.—published before the filing date of applicants' patent application.

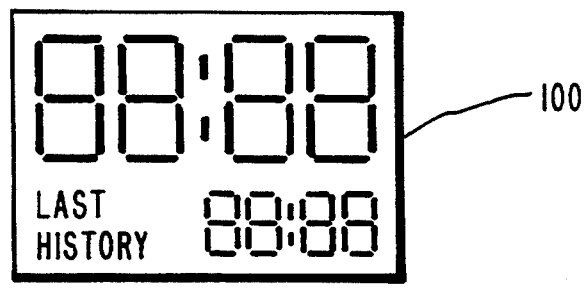
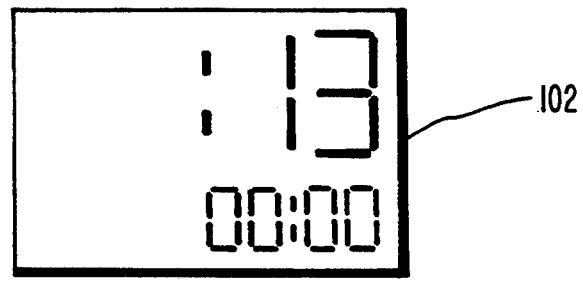
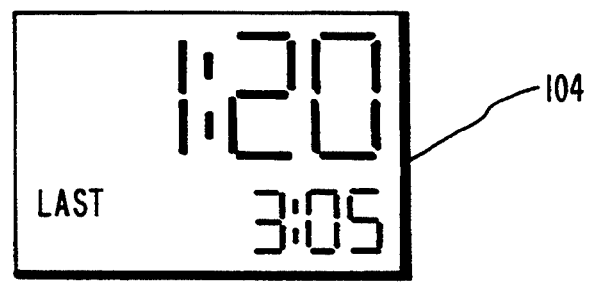
FIG. 3

SYRINGE APPARATUS WITH PRESSURE GAUGE AND DETACHABLE TIMER

RELATED APPLICATION INFORMATION

This application is a continuation-in-part of U.S. application Ser. No. 07/900,987 filed Jun. 18, 1992 now U.S. Pat. No. 5,259,838.

BACKGROUND OF THE INVENTION

1. Field of the Invention

The present invention relates to a syringe device used to inflate balloon-tipped catheters, such as coronary angioplasty dilatation catheters. More particularly, the present invention relates to a syringe apparatus having a pressure gauge and a detachable and reusable timer for measuring both the pressure generated by the syringe and the duration of the inflation or deflation event.

2. Background Information

An important tool in present medical procedures is the use of balloon-tipped catheters. Numerous configurations of balloon-tipped catheters have been developed for particular medical procedures. For purposes of simplicity and brevity, the following discussion will be directed to the use of a particular type of balloon-tipped catheter generally known as coronary angioplasty dilatation catheters.

Following the first primitive experiments in coronary angioplasty in the 1970s, coronary angioplasty quickly received widespread attention as an alternative to coronary bypass surgery. Coronary bypass surgery involves surgical access to the heart, placing the patient on an extracorporeal blood oxygenation system so that the heart can be stopped for surgery, and then surgically attaching one or more passageways to bypass a clogged coronary artery, all under a general anesthetic. Coronary angioplasty, generally performed under a local anesthetic, involves running a dilatation catheter (a catheter having an inflatable balloon near the end) to the diseased blood vessel and then inflating the balloon in order to open the passageway, thereby obtaining increased blood flow. The angioplasty procedure typically involves less risk to the patient, and significantly lessens the patient's discomfort and recovery time.

Of great importance during an angioplasty procedure is to take notice that during inflation of the dilatation catheter, no blood can flow through the blood vessel being mechanically dilated. Clearly, the disruption of blood flow must be limited in duration so as to avoid tissue damage due to oxygen deprivation. Hence, it is important to insure that the balloon is deflated and blood flow restored before tissue damage can occur. In most cases, it is not possible to adequately dilate a diseased blood vessel in a single inflation. In cases where it is necessary to undertake multiple inflations in the same location it is important to allow sufficient time between successive inflations so that the tissues fed by the diseased blood vessel can become fully oxygenated before blood flow is disrupted again.

At the same time, it is important to the success of the procedure that the dilation of the vessel be permitted to extend for a significant period of time. Although specific techniques can vary significantly depending upon the nature of the blockage, the catheter being used, and the like, the most common technique involves inflating the catheter relatively rapidly and then leaving it in place for several minutes. Although it might be proposed to use very short intervals of inflation in order to minimize the risk due to oxygen deprivation, followed by long intervals of deflation, it has been found to be better to utilize very long intervals of inflation in order to achieve the most effective dilation of the diseased blood vessel, and short intervals of deflation in order to bring the procedure to a conclusion more rapidly. The typical angioplasty procedure compromises these two factors by maintaining the balloon in the inflated and deflated conditions for a moderate amount of time.

In order to insure the success of the procedure without damage to the tissues fed by the diseased blood vessel, it is critical to monitor the duration of each inflation and deflation. It is also important that the physician performing the angioplasty have access to historical information regarding the duration of past inflations and deflations. In the past, this information has typically been recorded manually. Commonly, the operator of the syringe used to apply the inflation pressure will call out as pressure is applied and the time is noted by an assistant, or the assistant activates a stopwatch. The assistant continuously monitors the time and informs the catheterization team as required. At the appropriate time, as determined by the directing physician, the syringe operator deflates the catheter while the assistant monitors the deflation time. The assistant also maintains a record of the duration of each inflation and deflation. At any given time, the directing physician can learn of the duration of the most recent inflation or deflation, and the history of past inflations and deflations by asking the assistant.

Obviously, this process is somewhat cumbersome, and is also subject to errors in computing durations, while recording the information, or reporting it as required. This is particularly so when the assistant has other significant duties. Yet, it is quite expensive to dedicate an assistant solely for the function of monitoring and recording times.

One approach to dispensing with the function of the assistant in monitoring times has been to utilize computers to serve that function. For example, one approach has been to incorporate a pressure transducer into the syringe system used to inflate the balloon-tipped catheter. A computer is then used to monitor the pressure transducer to mark changes in pressure corresponding to inflation and deflation, and the duration of each such pressure change. The difficulty with this approach is that although very accurate and reliable, it is expensive, and some angioplasty facilities are unable to afford to purchase one. This approach also involves the use of yet another instrument, and some directing physicians are unwilling to add another instrument to the already very cluttered angioplasty operating theater. Despite the serious shortcomings of the original system using an assistant to monitor and record times of inflation and deflation, facilities and physicians finding themselves unable or unwilling to add a computerized monitor have had no alternatives.

SUMMARY OF THE INVENTION

It is a primary object of the present invention to provide a syringe apparatus and attached pressure gauge and timing mechanism enabling a syringe operator to monitor inflation and deflation times without the need for an assistant, yet without requiring purchase or use of computerized monitors.

It is another object of the present invention to collect a record of inflation and deflation times which may be easily reviewed, without requiring an assistant to manually record such information.

Yet another object of the present invention is to provide a relatively low cost syringe apparatus capable of use by a single person to control and monitor inflation and deflation pressures and durations.

An additional object of the present invention is to further reduce the overall cost of the syringe apparatus by providing a syringe that utilizes a detachable and reusable timing mechanism.

Additional objects and advantages of the invention are set forth hereinbelow in the detailed description, or will be appreciated by the practice of the invention.

To achieve the foregoing objects, and in accordance with the invention as embodied and broadly described herein, a syringe apparatus is provided which is adapted for use with balloon-tipped catheters. In one presently preferred embodiment, the syringe apparatus of the present invention is advantageously provided with a syringe assembly capable of generating pressures sufficient to inflate the balloon-tipped catheter, and also a pressure gauge and a timer assembly. In one mode, a presently preferred timer assembly displays the duration of a current event of inflation or deflation, and the duration of the most recent past event of inflation or deflation. In another mode, the timer assembly displays historical information showing the event number and duration of past events of inflation and deflation. The pressure gauge display and the timer assembly display are situated conveniently on the syringe assembly and in proximity to one another so as to enable a syringe operator to substantially simultaneously monitor durations of inflation and deflation without the need for an assistant, yet without requiring purchase or use of computerized monitors.

In yet another presently preferred embodiment of the invention, the timer assembly is incorporated into a detachable and reusable module, which can be detachably mounted to a housing on the syringe assembly. In this manner, a single detachable timer module can be reused for numerous procedures, thereby saving the cost of having to purchase a separate timer for each syringe assembly. In another mode, the pressure gauge is mounted to the detachable timer module thereby allowing the pressure gauge to also be detached and reused with different syringe assemblies.

BRIEF DESCRIPTION OF THE DRAWINGS

In the accompanying drawings, which represent the best mode presently contemplated for carrying out the present invention:

FIG. 3 is a series of views of the display used in connection with the timing of inflation and deflation events;

DETAILED DESCRIPTION OF THE PREFERRED EMBODIMENT

The present invention is directed to a syringe apparatus having an attached pressure gauge and a timing mechanism which will enable a syringe operator to simultaneously monitor inflation and deflation pressures and durations of inflations and deflations.

Figure 1:
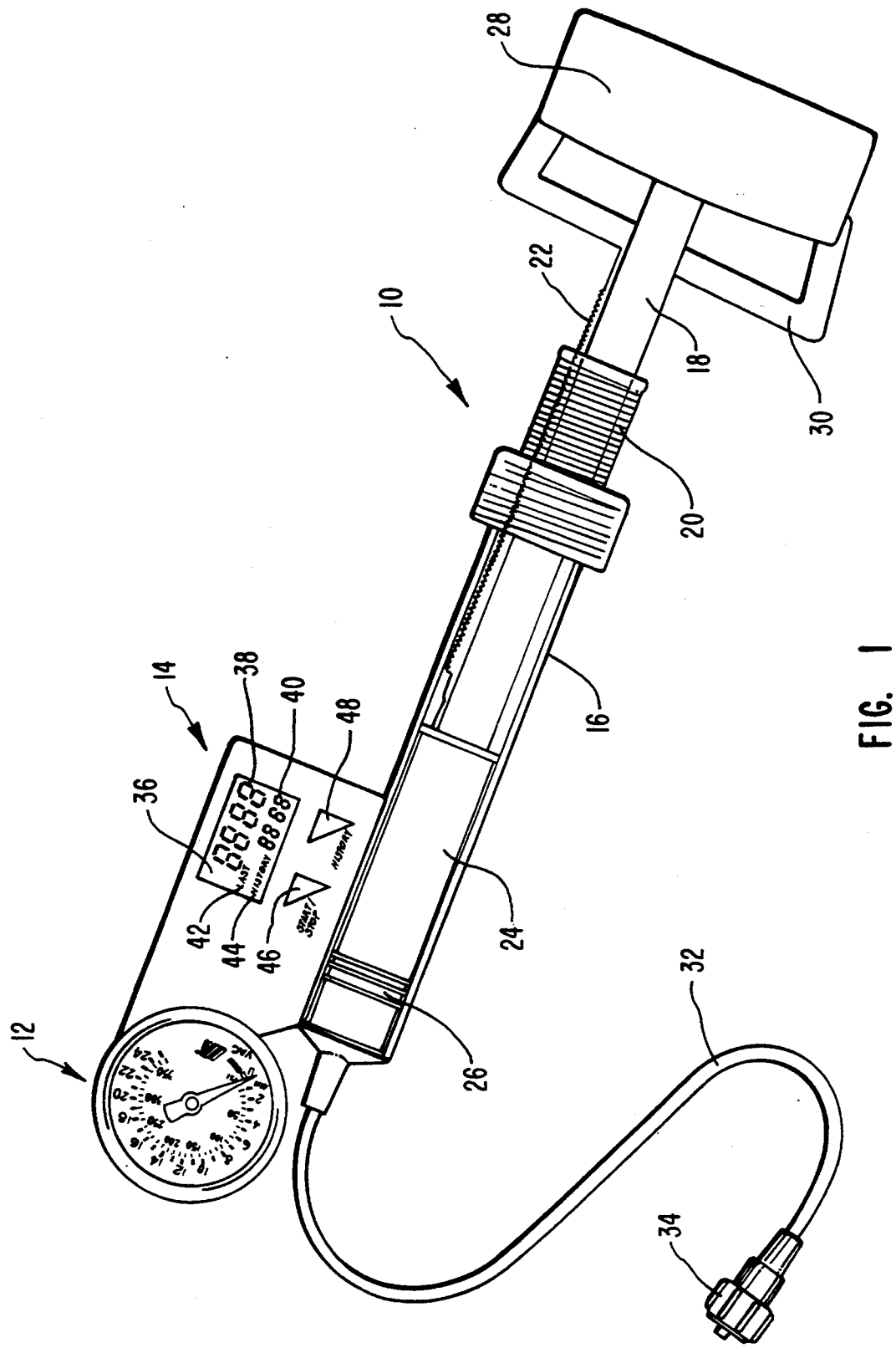
FIG. 1 is a perspective view of one presently preferred embodiment of a syringe apparatus in accordance with the present invention for use in inflating a balloon-tipped catheter.

Reference is first made to FIG. 1, which illustrates one presently preferred embodiment of a syringe apparatus constructed in accordance with the present invention. The syringe apparatus of FIG. 1 includes a syringe assembly, shown generally at reference numeral 10, a pressure gauge, shown generally at 12, and a timer assembly, shown generally at 14.

The syringe assembly is comprised of a syringe barrel 16 and a plunger 18. Syringe barrel 16 is preferably constructed of a clear polycarbonate, medical grade plastic material. Preferably, plunger 18 is also constructed of medical grade plastic material, though typically of an opaque nature.

Syringe barrel 16 is preferably provided with internal threads 20 adapted to engage with corresponding threads 22 on one side of plunger 18. Plunger 18 is slidably operative within syringe barrel 16. The distal end of plunger 18 is advantageously provided with a collar 24 fitted with a rubber tip 26 which provides a fluid-tight seal about the periphery of the barrel so that fluid can be expelled from the syringe barrel 16 through pressure tubing 32 and luer fitting 34 as plunger 18 is advanced into syringe barrel 16. During procedures involving a balloon-tipped catheter, luer fitting 34 is connected to the input end of such a catheter, so that fluid expelled from the syringe barrel 16 will inflate the balloon of the balloon-tipped catheter.

The proximal end of plunger 18 is preferably provided with a handle 28 and a trigger mechanism 30. Trigger mechanism 30 is connected to plunger threads 22, so that compression of trigger mechanism 30 towards handle 28 serves to disengage plunger threads 22 from engagement with barrel threads 20. When plunger threads 22 and barrel threads 20 are disengaged, plunger 18 is free to slide in or out of syringe barrel 16 through application of force by the operator of the syringe assembly. As soon as the operator releases trigger mechanism 30, plunger threads 22 will reengage barrel threads 20, thereby securing the plunger in position. Fine adjustments to the position of plunger 18 within syringe barrel 16 may be made by rotating the plunger clockwise or counterclockwise in a screwing motion. In this manner, fluid pressures can be quickly exerted and/or released as desired, but provision is also made for very precise adjustment of pressures by slowly screwing plunger 18 into or out of syringe barrel 16.

It is to be understood that the nature and mechanical aspects of the syringe assembly 10 are not limited to those specific features illustrated in FIG. 1, and that a variety of different types of syringe designs could be utilized without departing from the spirit and scope of the present invention. The particular syringe apparatus as illustrated in FIG. 1 is presently preferred, however. Its design is more particularly described in U.S. Pat. Nos. 5,047,015 and 5,057,078, both of which are incorporated herein by reference.

In the presently preferred embodiment illustrated in FIG. 1 and described herein, the timer assembly is adapted to perform two different functions: the first function being the display of the elapsed time of an ongoing inflation or deflation in real time while simultaneously displaying the total duration of the most recent preceding event of inflation or deflation; and the second function being the display of historical data of earlier events of inflation and deflation.

In order to present the information required in the performance of these two functions, timer assembly 14 is advantageously provided with a display 36 providing a visual readout of timer assembly data. Display 36 has two separate data readout areas, large numerals 38 and small numerals 40. As described more fully hereafter, large numerals 38 are used with respect to the first function to display the current duration of inflation and deflation in real time, and small numerals 40 are used to display the total duration of the most recent preceding event of inflation or deflation. With respect to the second, historical, function, large numerals 38 are used to depict the duration of a preceding event of inflation or deflation, and the small numerals 40 are used to identify which event is being displayed. For purposes of assisting the syringe operator to recognize which display is being viewed at any given moment, display 36 is also provided with two indicators: a "last" indicator 42, and a "history" indicator 44. "Last" indicator 42 is displayed during the timing of a current event, whereas "history" indicator 44 is displayed during the display of data relating to preceding events. Display 36 is preferably constructed from backlit liquid crystal display (LCD) components, although it will be appreciated that any display capable of running off of battery power could be substituted for LCDs.

The timer assembly is activated by use of an on/off switch (not shown), preferably located on the side of assembly 14. As described below, the initial operation of the on/off switch initializes timer assembly 14 and prepares it for timing of the first event in the inflation/deflation cycle of events. Activation of start/stop button 46 then initiates timing, and each succeeding activation of start/stop button 46 ends the timing of a current event, and commences timing of the next event. Timer assembly 14 is also provided with history button 48, used to access historical data. The provision of a start/stop button 46 and history button 48 lends the embodiment of FIG. 1 to being labeled a "2 button" embodiment.

Figure 2:
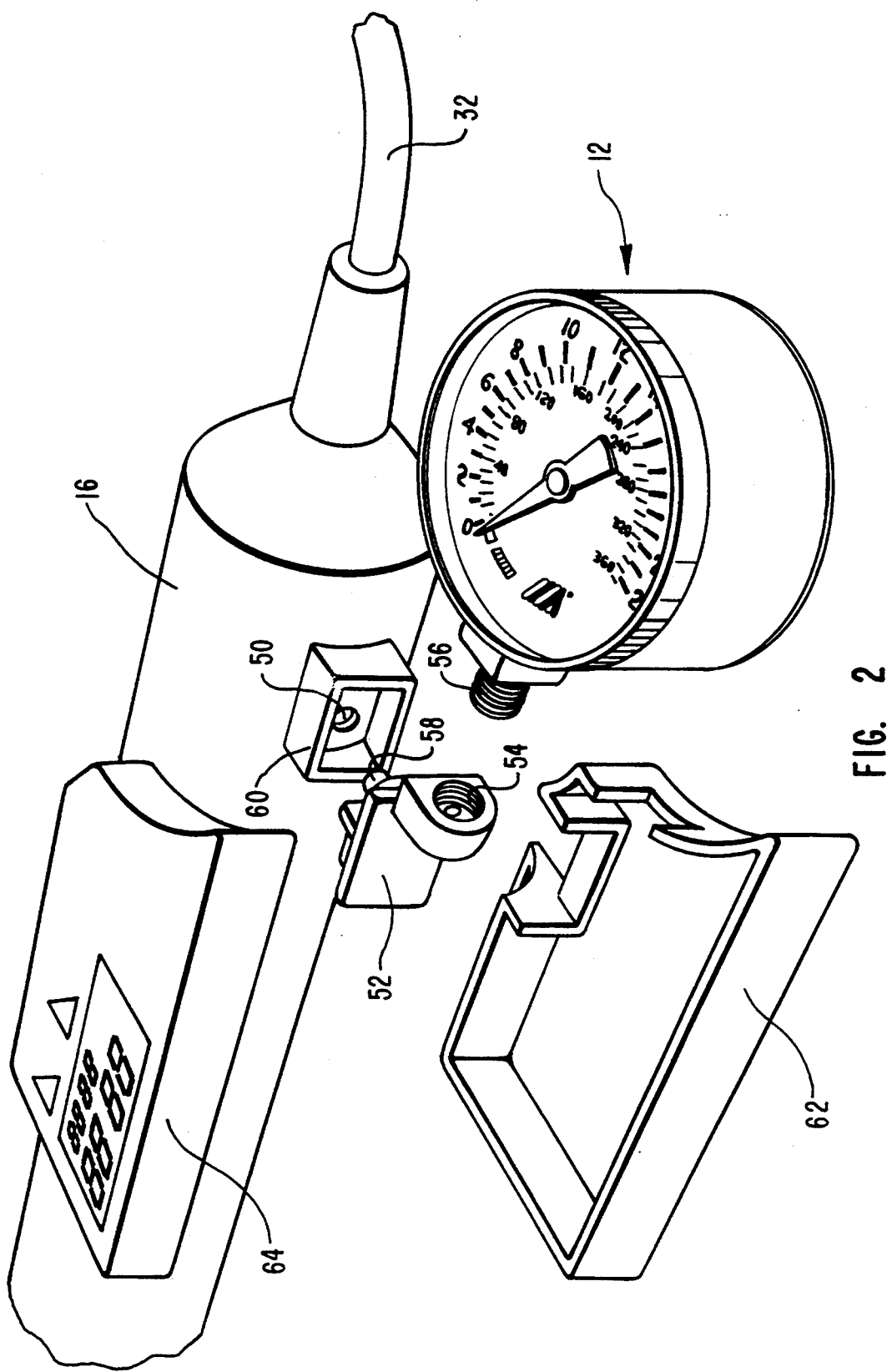
FIG. 2 is a partially exploded view of the syringe apparatus of FIG. 1, illustrating how the pressure gauge is interfaced to the syringe assembly in the presently preferred embodiment of the invention.

Referring now to FIG. 2, pressure gauge 12 of the presently preferred embodiment communicates with the interior of the syringe barrel 16 through a port 50. The pressure gauge 12 is coupled to port 50 through use of a fitting 52 having threads adapted for engagement with threads 56 of the pressure gauge in a fluid-tight manner. Fitting 52 is provided with a projection 58 adapted to mate with port 50. A housing well 60 attached to syringe barrel 16 or formed integrally therewith provides support to fitting 52 as well as to the bottom housing 62 and top housing 64 of the timer assembly. It will be appreciated that fitting 52 must be secured to port 50 in fluid-tight fashion, and that an appropriate adhesive should be used so as to insure the structural integrity of the syringe apparatus.

For use, the apparatus of the present invention is attached to a balloon-tipped catheter, such as an angioplasty catheter, in a conventional fashion. As soon as the directing physician calls for the first inflation, the syringe operator presses start/stop button 46 with his or her left thumb or other finger and then, after momentarily observing the timer assembly to insure it does not give out an error reading, advances plunger 18 within syringe barrel 16 with the operator's right hand while monitoring pressure gauge 12. An experienced syringe operator can easily and rapidly advance the plunger within the syringe barrel until the desired pressure is reached, thereby inflating the balloon the desired amount. It may be advantageous, however to provide markings (not shown) on the side of syringe barrel 16 to provide a reference for the syringe operator.

Figure 4:
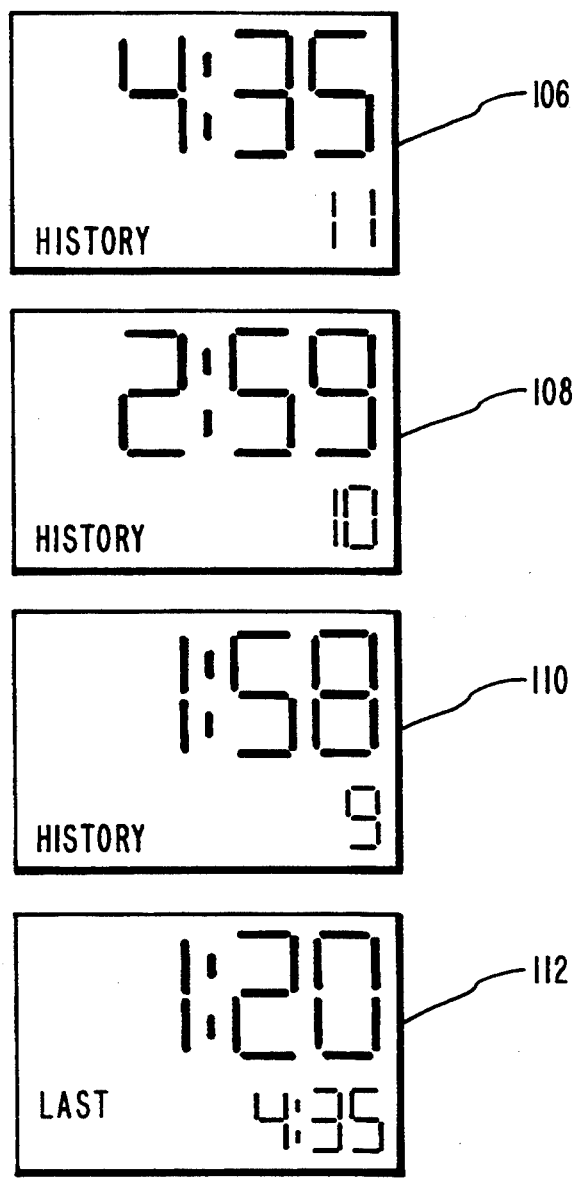
FIG. 4 is a series of views of the display used to present historical durations of various inflation and deflation events.

For purposes of discussion regarding the use and operation of the present invention, several events are illustrated in FIGS. 3 and 4. Each of these events depicts the display at a momentary instant of time during use of the invention, which for purposes of simplicity shall sometimes hereinafter be referred to as a "display condition."

With reference to FIG. 3, activation of the on/off switch causes initialization, observed as a momentary illumination of all segments of the liquid crystal display, shown generally as display condition 100. As soon as start/stop button 46 is activated, timer assembly 14 commences timing the first inflation event. Display condition 102 depicts the timer display 36 at a time 13 seconds after the start/stop button was first activated. Small numerals 40 will show a "zero" reading during the first inflation event, since there is no earlier event to report. At any given moment during this first inflation event, the directing physician may easily determine the duration of inflation by either asking the syringe operator or observing the timer assembly display himself or herself. Importantly, the syringe operator can monitor the time continuously without having to look away from the field of view directed at the pressure gauge.

At the appropriate time, which might be predetermined or might be determined from observations made during the course of a medical procedure involving a balloon-tipped catheter, the directing physician will instruct the syringe operator to commence deflation. Trigger mechanism 30 is retracted into handle 28, thereby disengaging plunger threads 22 from barrel threads 20, and the operator quickly retracts plunger 18 while restraining syringe barrel 16 in his or her other hand, thereby withdrawing fluid from the now-filled balloon at the tip of the balloon-tipped catheter, and thereby deflating the balloon. At about the same time, the operator activates start/stop button 46 to mark the end of the first event (inflation), and the commencement of the second event (deflation).

Display condition 104 depicts the situation one minute and 20 seconds after the start of the second event (deflation). It also depicts by the small LCD numerals the duration of the "last" event as having been 3 minutes 5 seconds. Hence, the syringe operator is able to monitor the current time of deflation and also observe the preceding duration of inflation.

As the start/stop button is activated at the commencement of each succeeding event (inflation or deflation), the total duration of the immediately preceding event is displayed as the "last" event by the small LCD numerals, and the current duration of the current event is displayed by the large LCD numerals.

An additional feature of the "2 button" timer is the ability to review the "history" of past events (inflation and deflation). This feature is useful at the conclusion of the procedure in order to prepare a permanent record of the durations of inflations and deflations, and is also useful in circumstances where the directing physician has a question regarding previous inflation and/or deflation events.

The "history" function is accessed by activating history button 48. FIG. 4 depicts several display conditions which serve to illustrate the use of the history function of the presently preferred embodiment of the timer assembly of the present invention. Display condition 106 depicts a fictional reading which a syringe operator might observe during the course of an angioplasty procedure by pressing and holding down the history button. Display condition 106 shows that the immediately preceding event was event number 11, and that the duration of event number 11 was 4 minutes 35 seconds. While continuing to depress the history button 48, earlier events may be reviewed by repeatedly pressing the start/stop button 46. Display condition 108 depicts a fictional display after the syringe operator has pressed the start/stop button a single time. It shows that event number 10 had a duration of 2 minutes 59 seconds. Pressing start/stop button 46 again calls up the information stored for event number 9: display condition 110 shows that event number 9 had a duration of 1 minute 58 seconds. The durations of additional historical events may be accessed in similar fashion by additional activations of start/stop button 46, while continuing to depress history button 48.

The 2 button embodiment of timer assembly 14 does not display whether a current or historical event is an inflation or deflation. It is easy for one to read the data from the historical readout information, however, because inflations and deflations occur alternately, commencing with an inflation. Hence, in normal circumstances, each odd numbered event represents an inflation, and each even numbered event represents a deflation. It should be appreciated that a display indicating whether an event is an inflation or deflation could be added, wherein the label would alternate between "inflation" and "deflation" with each operation of the start/stop button.

As soon as the review of historical data is complete, the syringe operator releases history button 48. Display condition 112 illustrates that once this occurs, the timer assembly of the presently preferred embodiment reverts to tracking the current event and displaying the duration of the immediately preceding event. As shown in display condition 112, the current event has proceeded for 1 minute 20 seconds, and the last event had a duration of 4 minutes 35 seconds (which as noted in display condition 106, was event number 11).

From the foregoing, it will be appreciated that the 2 button syringe apparatus illustrated in FIGS. 1 and 2 solves the problems of conventional systems requiring either an additional assistant to monitor and record time information, or an expensive computer system. The syringe operator may easily and safely handle the task of timekeeping as well as controlling the syringe pressures and effecting the inflations and deflations of the balloon-tipped catheter.

Figure 5A:
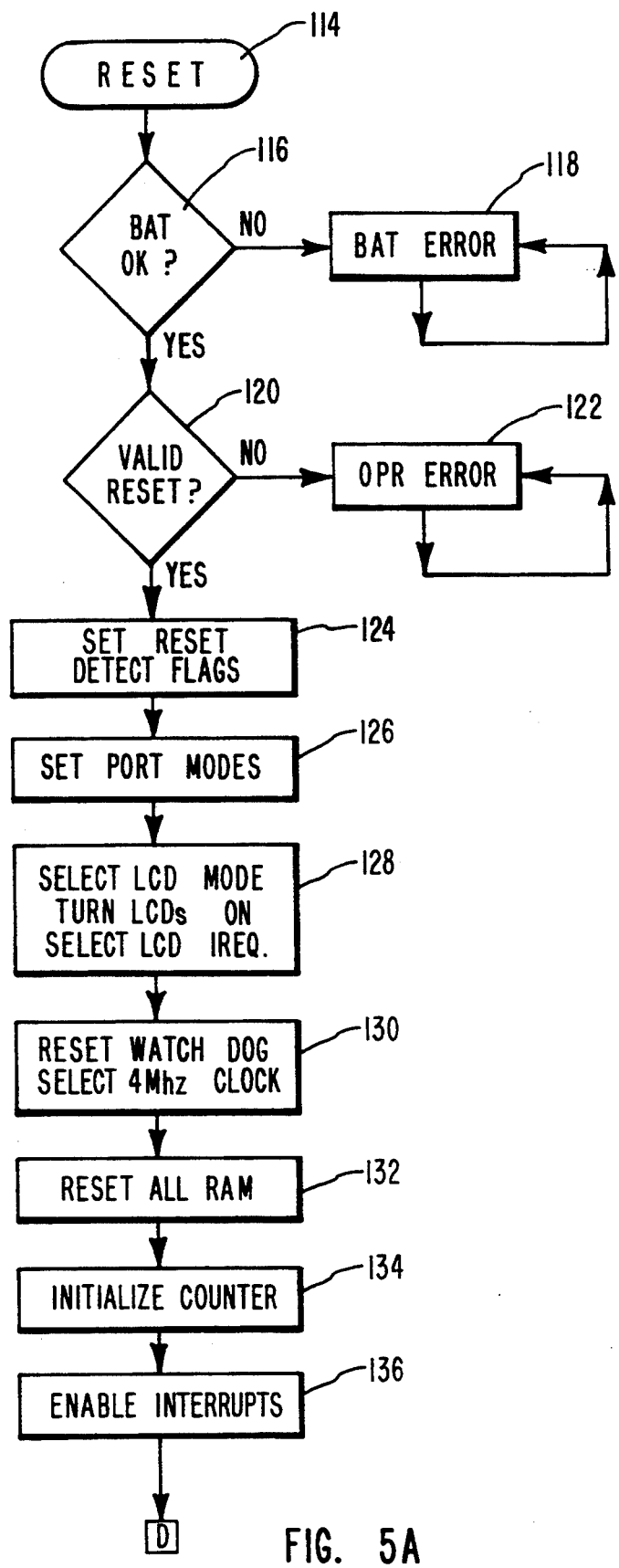
FIGS. 5A, 5B and 5C comprise a flow chart showing the flow of operations of the presently preferred timer assembly of the embodiment illustrated in FIG. 1.
Figure 5B:
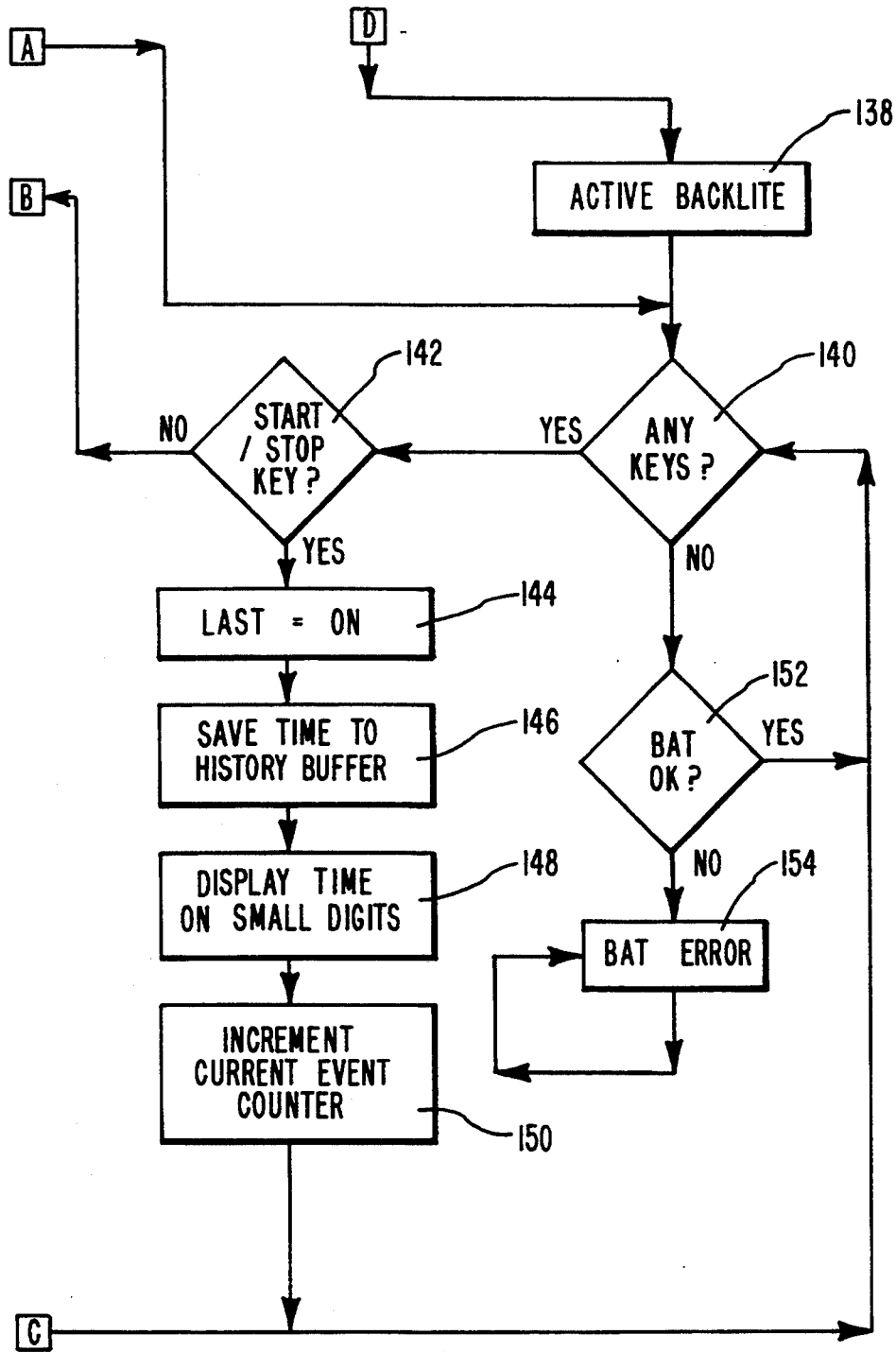
Figure 5C:
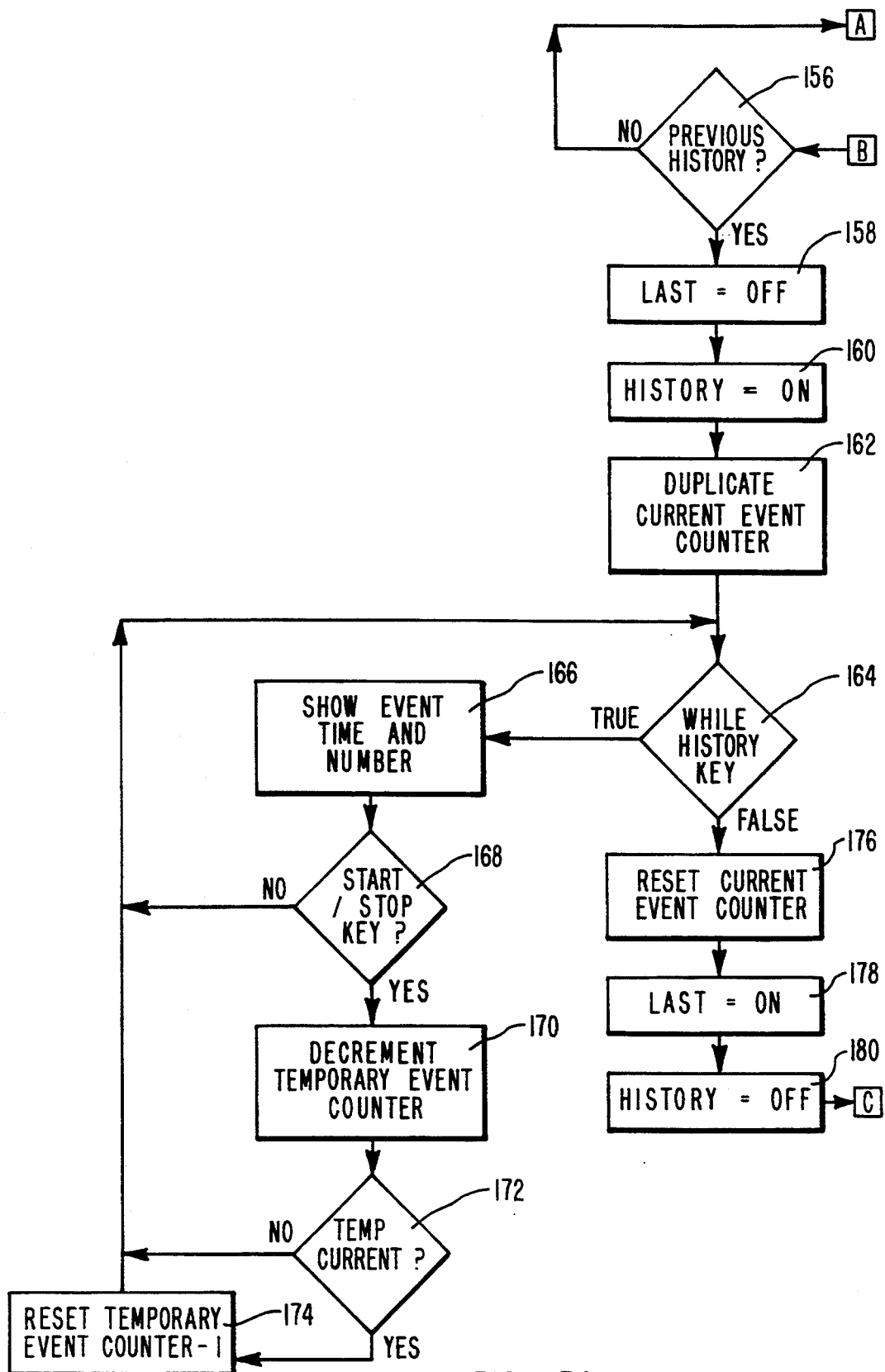

A flow chart of the presently preferred 2 button timer assembly 14 is illustrated in FIGS. 5A, 5B and 5C. Commencing with FIG. 5A, the flow of operations begins at step 114, depicted as "reset", which commences upon activation of the on/off switch at the commencement of the medical procedure involving the balloon-tipped catheter. The first step performed upon "reset" is testing the battery, shown at step 116. If not, a battery error condition 118 will prevent the timer assembly from operating. This is important because it would clearly be very disadvantageous for a battery to run down during an angioplasty or other balloon-tipped catheter procedure.

In the typical situation where the battery checks out satisfactorily, the next step 120 involves checking whether the reset was valid; if not, another error condition 122 is encountered, again preventing commencement of the medical procedure. Where the reset was valid, a series of steps quickly follow: a reset detect flag is set (step 124); port modes are set (step 126); the liquid crystal displays are activated (step 128); a Watch Dog is set, using a 4.19 megahertz clock (step 130); RAM memory is reset (step 132); the counter is reset (step 134); system interrupts are enabled (step 136); and the LCD backlighting is activated (step 138, shown by following icon "D" from the bottom of FIG. 5A to the top of FIG. 5B).

Upon activation of the start/stop button 46, the timer commences incrementing the current duration of event number 1 (as depicted in display condition 102 of FIG. 3), while monitoring for activation of either the start/stop button or the history button, and simultaneously monitoring the battery condition (steps 152 and 154). Step 140 depicts this operation.

If the start/stop button 46 is activated, step 142 initiates a series of steps involving activation of the "last" indicator (step 144); saving the duration of the most recent event in a history buffer (step 146); displaying the time of the most recent event on the small LCD display (step 148); and incrementing the current event counter (step 150). Flow then reverts to step 140 for continued incrementation of the duration of the current event in the large LCD display while monitoring the battery condition (steps 152 and 154) and monitoring for further activation of either the start/stop button or the history button.

Step 156 (following the "B" icon from FIG. 5B to FIG. 5C) commences the flow of operation upon activation of history button 48: the "last" indicator is deactivated (step 158); the "history" indicator is activated (step 160); the current event counter is checked (step 162); and the status of the 48 history button (activated or not activated?) is monitored (step 164). If the history button remains activated, the LCD displays the preceding event number and duration (step 166), then monitors the condition of the start/stop button (activated or not)(step 168). If the start/stop button remains inactivated and the history button remains activated, the timer waits for any change in status of either key. If start/stop button 46 is activated, the temporary event counter is decremented (step 170) and tested (steps 172 and 174). If at some point the history button is no longer activated, step 164 changes the flow away from step 166 and moves to step 176, which involves resetting the current event counter, activates the "last" indicator (step 178), and deactivates the "history" indicator. Flow then reverts once more back to step 140 (following icon "A").

It may in some circumstances be desirable to include additional features to the basic "2 button" timer assembly 14 described in detail above, or in other circumstances to provide fewer features. In order to demonstrate alternative embodiments within the basic teachings of the present invention, following is a discussion of a "3 button" timer assembly and a "1 button" assembly.

Figure 6:
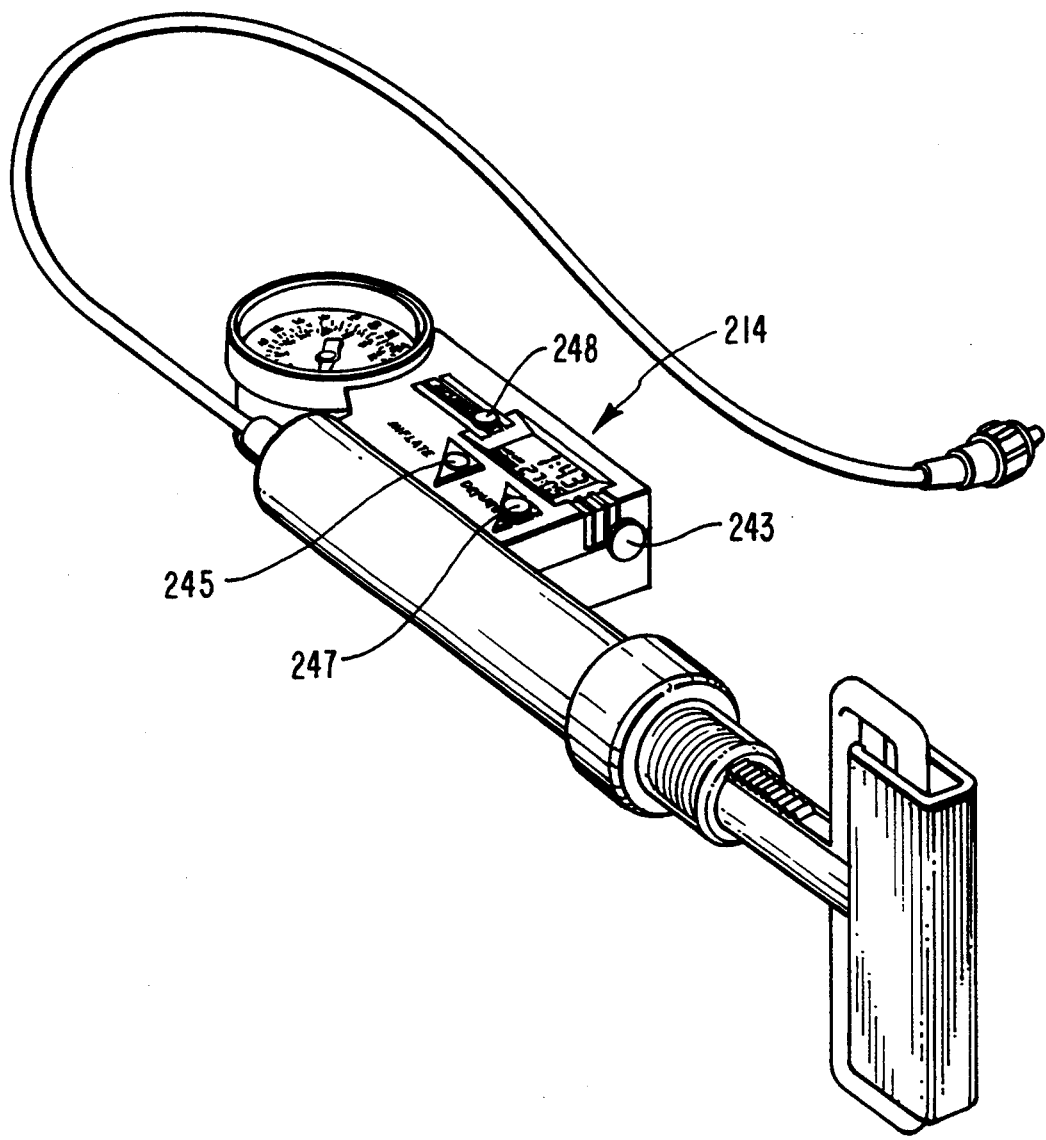
FIG. 6 is a perspective view of a second embodiment of the syringe apparatus of the present invention.

FIG. 6 depicts another presently preferred syringe apparatus in accordance with the present invention, this embodiment having a "3 button" timer assembly, shown generally by reference numeral 214. As with timer assembly 14, timer assembly 214 is advantageously provided with a "history" button 248. The "start/stop button" 46 of timer assembly 14, is replaced in timer assembly 214 by "inflate" button 245 and "deflate" button 247.

After applying battery power to the timer assembly 214 by actuating on/off button 243, the timer assembly may be activated by pressing inflate button 245. This starts timing of the first inflation event, and activates a label on the LCD screen indicating that the timer assembly is timing an inflation event. Timing continues until the syringe operator presses the deflate button 247. As would be expected, pressing deflate button 247 resets the timer and commences timing of the first delation event, and activates a label on the LCD display indicating that the timer assembly is timing a deflation event. The first inflation duration is saved to a buffer, which in the preferred embodiment will store up to 16 inflation and deflation events, although it will be appreciated that more or less buffer storage may be provided. Each subsequent activation of the inflate and deflate buttons moves the duration of the preceding event into the buffer, and commences timing of the current event. Each successive activation of the inflate or deflate button also increments a counter, which preferably is capable of incrementing up to 64 events.

In order to prevent errors such as consecutive "inflations", the timer is advantageously programmed so that the inflate button has no further effect during an inflation, and the deflate button has no effect during a deflation. Hence, pressing inflate button 245 during the course of an inflation event will be ignored by timer assembly 214. Likewise, pressing deflate button 247 during the course of a deflation will have no effect.

Historical information may be accessed through use of history button 248. While pressing and holding the history button, pressing either the inflate button or the deflate button scrolls back one event.

Figure 7:
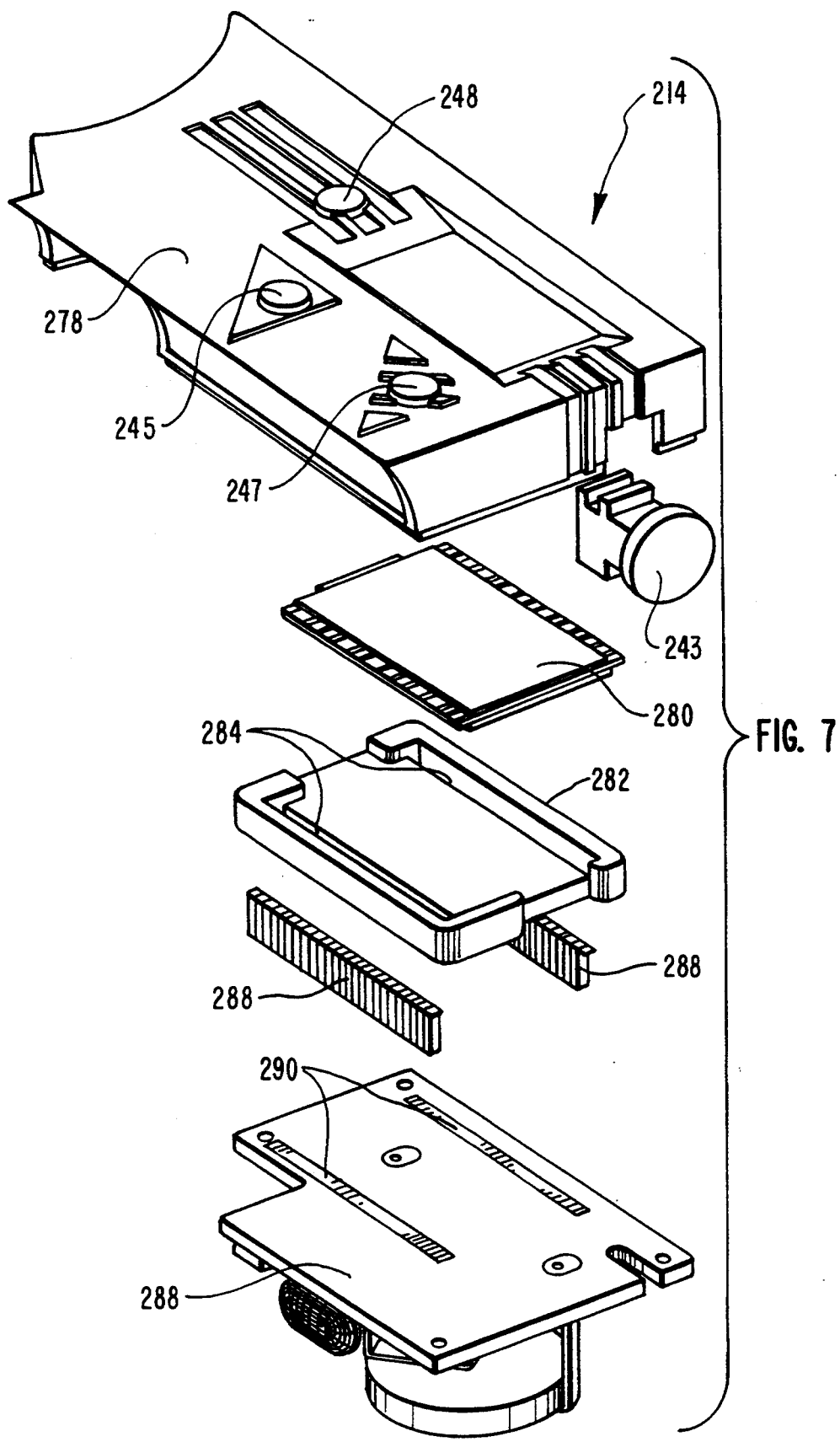
FIG. 7 is an exploded view of a portion of the timer assembly of the embodiment shown in FIG. 6.
Figure 8:
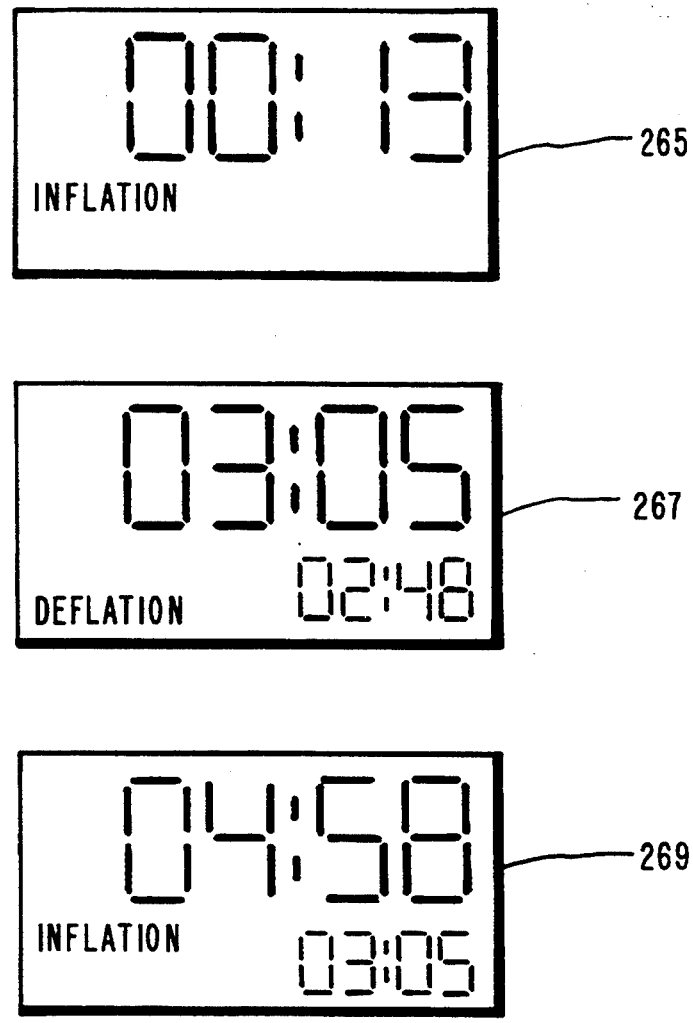
FIG. 8 is a series of views of the display of the three button timer assembly of FIG. 6 at various times during a fictitious use of that assembly.

FIG. 8 illustrates several fictitious events using the 3 button timer assembly of FIG. 7. Display condition 265 illustrates an inflation event at a moment 13 seconds after it was initiated. It should be noted that the label "inflation" appears on the LCD display to indicate that an inflation is in process. By virtue of the fact that no information is displayed below the large numerals, a user will know that this is the first inflation event. Display condition 267 indicates a deflation event which has continued for 3 minutes, 5 seconds. The small numerals show that the preceding inflation event had a total duration of 2 minutes, 48 seconds. Display condition 269 depicts the next succeeding inflation event, indicating the current duration of deflation is 4 minutes, 58 seconds. The duration of the preceding deflation was 3 minutes, 5 seconds.

Figure 9:
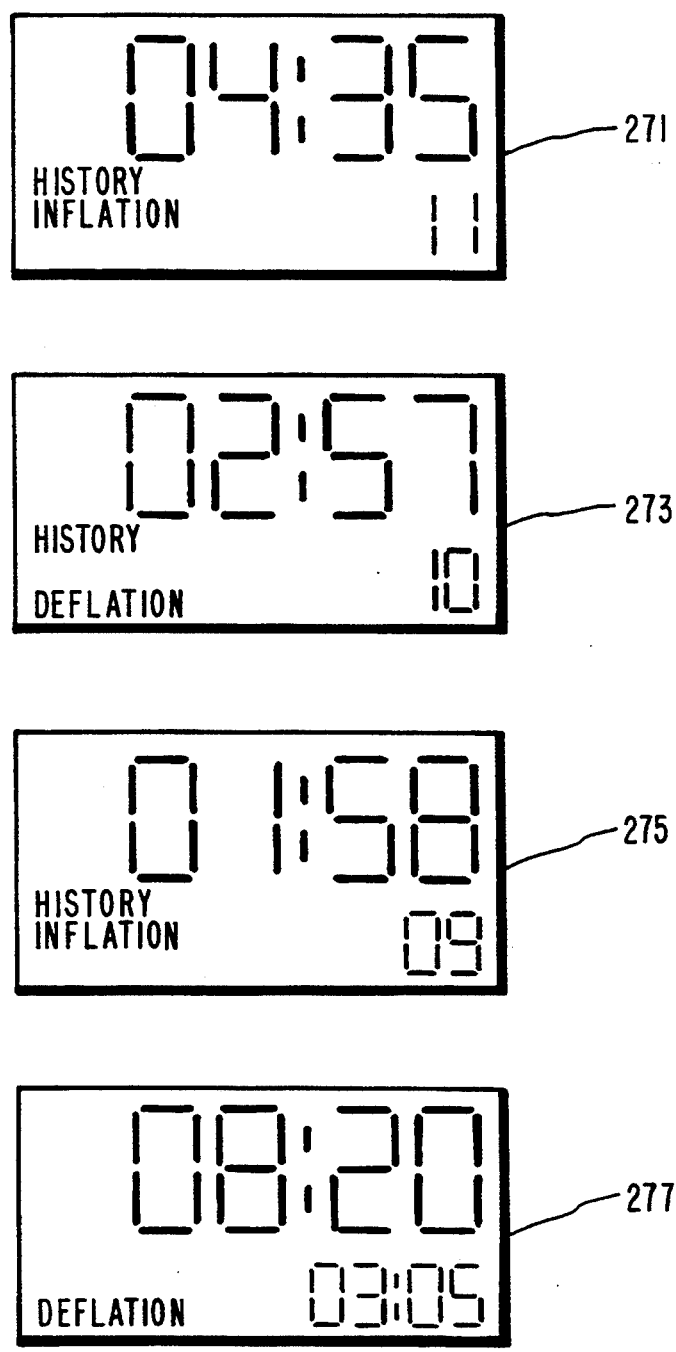
FIG. 9 is a series of views of the display of FIG. 8 showing how historical information may be viewed.

FIG. 9 illustrates the ability to review historical information. Upon pressing and holding the history button, the duration of the immediately past event is displayed. Display condition 271 indicates that event 11 was an inflation having a duration of 4 minutes, 35 seconds. Pressing either the inflate button 245 or deflate button 247, while continuing to hold history button 248, decrements the history buffer to the previous event. Thus, display condition 273 shows deflation event 10 had a duration of 2 minutes, 57 seconds. Pressing either the inflation or deflation button again results in display condition 275, which indicates that inflation event 9 had a duration of 1 minute, 58 seconds. Finally, releasing the history button returns the current event timer, as indicated at display condition 277, where the current deflation event has a current duration of 8 minutes, 20 seconds, and the duration of the preceding inflation event may be seen to have been 3 minutes, 5 seconds.

A presently preferred construction of a timer assembly in accordance with the present invention is illustrated in FIG. 7, which is an exploded view of a portion of timer assembly 214 of FIG. 6. Liquid crystal display 280 is shown immediately below top cover 278. The sides of LCD 280 are shown as comprising a series of electrical contacts which serve to activate the various segments of the display.

Below the LCD is a diffuser 282, which is preferably molded in a one piece structure from a generally transparent plastic. Diffuser 282 serves to backlight and support the LCD. Diffuser 282 has a pair of opposing slots 284 which lie along the length of the LCD electrical contacts, thereby leaving those contacts exposed. Lying below diffuser 282 is an electronic timer module 288, which includes the electronic components of timer assembly 214 and the battery to operate them. A pair of electronic contact strips 290 lie along the surface of timer module 288, corresponding in position to the LCD electrical contacts.

Advantageously, from a manufacturing standpoint, a pair of "zebra" pads 288 are provided for placement between strips 290 and the LCD electrical contacts. Zebra pads 288 are constructed as a composite of small blocks of insulating material and conductive material, and are capable of carrying current from pads 290 to the LCD without mechanical connections. Zebra pads 288 extend through slots 284, and are held in place by the boundaries thereof.

Figure 10:
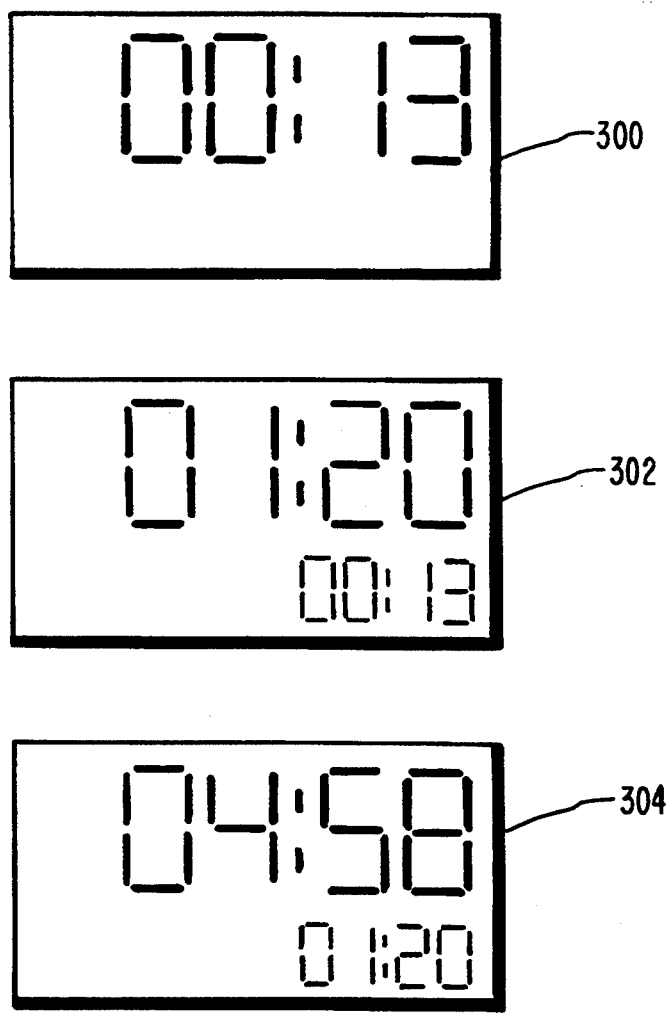
FIG. 10 is a series of views of a display which might be used in connection with a single button timer assembly.

As indicated above, it is also possible to provide a "1 button" timer assembly. Although not illustrated, the function of a 1 button embodiment will be readily understood from the disclosure set forth above. Unlike the 2 button and 3 button timer assemblies, it is currently contemplated that it might in some instances be less important to provide access to multiple historical events. Rather, it may be adequate in some circumstances to provide a timer assembly which shows the duration of the current event, and the duration of the immediately past event. These functions can be provided by a single button timer assembly, the single button being used to terminate timing of a current event, and commencing timing of the next succeeding event. Referring now to FIG. 10, display condition 300 illustrates a convenient display which might be used for a one button timer assembly. It shows an initial event having a total elapsed duration of 13 seconds. Upon activation of the control button, display condition 302 illustrates that the 13 second duration of that event will be displayed in small numerals on the LCD, while the large numerals depict the timing of the current event. Display condition 304, in turn shows a current elapsed time of 4 minutes, 58 seconds for the current event, and a historical duration of 1 minute, 20 seconds for the immediately past event.

FIGS. 11 through 14 illustrate yet another embodiment of the syringe apparatus. In the embodiments of FIGS. 11–14, rather than being permanently mounted to the syringe barrel, the timer assembly is detachably mountable to the syringe barrel and is thus reusable. Because the electronic timer assembly can be reused for numerous procedures, the overall cost of each angioplasty procedure is further reduced.

Figure 11:
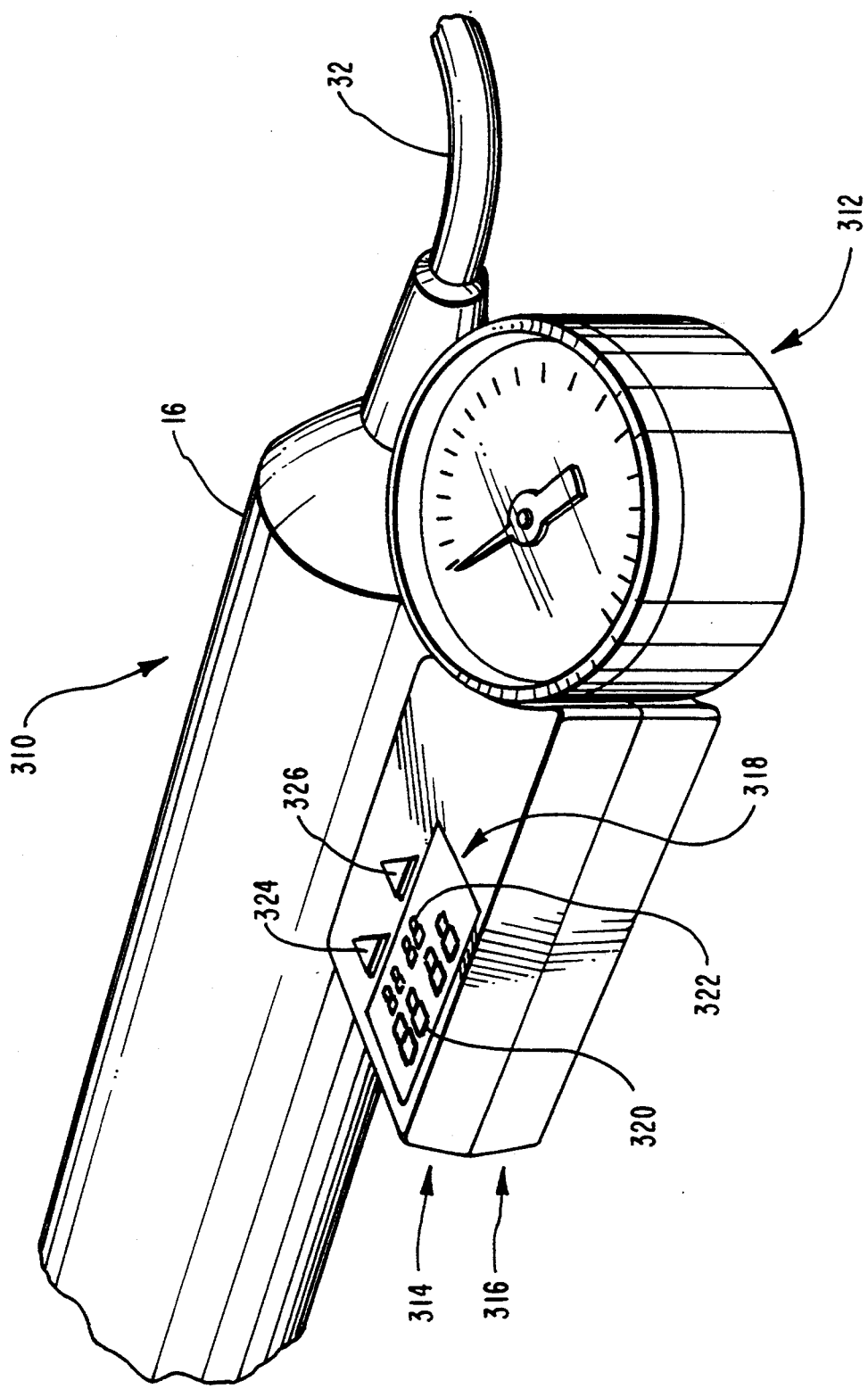
FIG. 11 is partial perspective view of another presently preferred embodiment of a syringe apparatus, wherein the timer assembly is detachable from the syringe barrel.

As is shown in FIG. 11, the syringe apparatus of this embodiment includes a syringe means for generating sufficient pressure to inflate a balloon-tipped catheter, as for example a syringe assembly, partially shown in FIG. 11 and designated generally as 310. The preferred syringe assembly 310 of this embodiment is similar in essentially all respects to the syringe assembly 10 discussed above in conjunction with FIG. 1 and that discussion will not be repeated here.

The syringe apparatus of FIG. 11 further includes a pressure gauge means for measuring and displaying the pressure generated by the syringe means, as for example a conventional strain gauge shown generally as 312. It should be appreciated that the preferred embodiment is illustrative only and is not to be construed as limiting the scope of the invention. For example, the pressure gauge means may also be comprised of an electronic pressure gauge used in conjunction with a piezoresistive semiconductor transducer and have a digital pressure readout, and still be within the intended scope of the present invention.

In the preferred embodiment of FIG. 11, the pressure gauge 312 is permanently affixed to the syringe assembly 310 in a manner so as to be in fluid communication with the interior of the syringe barrel 16. As used herein, the term "fluid communication" is intended to mean the pneumatic or hydraulic transmission (direct or indirect) of fluid pressures exerted within the syringe barrel 16 and the pressure tubing 32 to the pressure gauge means so that such fluid pressures can be sensed by the pressure gauge means. Direct transmission of such fluid pressures would occur, for example, when a strain gauge is placed in direct contact (either pneumatically or hydraulically, or a combination of both) with a fluid contained in a closed system, as would be the case in the preferred embodiment illustrated in FIG. 11. Indirect transmission could be said to occur, for example, where the pressure gauge means is coupled to a diaphragm that in turn contacts the fluid contained in a closed system.

As is further illustrated in FIG. 11, placed in close proximity to the pressure gauge 312 is a detachable timer means, as for example a detachable timer assembly 314, for measuring durations of separate events of inflation and deflation of the balloon tipped catheter. In FIG. 11, the detachable timer assembly 314 is illustrated as being in attached mode, and at the completion of the procedure can be detached for reuse with another syringe assembly 310.

As with the timer assembly of FIG. 1, the preferred embodiment of the detachable timer assembly 314 illustrated in FIG. 11 is adapted to perform two different functions: displaying the elapsed time of an ongoing inflation or deflation in real time while simultaneously displaying the total duration of the most recent preceding event of inflation or deflation; and displaying historical data of earlier events of inflation and deflation.

To present this information, FIG. 11 illustrates that in one presently preferred embodiment, the detachable timer assembly 314 includes a display means, shown as comprising a liquid crystal display 318, for visually displaying the time durations measured by the timer assembly 314. It will be appreciated that the display means may be comprised of any one of a number of displays well known in the art that are capable of running off of battery power. The display 318 preferably has two separate data readout areas, large numerals 320 and small numerals 322. These two separate readout areas 320,322 are similar in all respects to the data readout areas 38 and 40 discussed in conjunction with FIG. 1 above, and present the same timing information as that particular embodiment. That discussion will not be repeated here.

FIG. 11 also shows that in one presently preferred embodiment, the detachable timer assembly 314 has a first actuating means for commencing the timing of the duration of each successive event of inflation and deflation, as for example a start/stop button 324. In addition, there is a second actuating means for causing the display means to display the historical duration of each event of inflation and deflation previously performed, such as a history button 326. The start/stop button 324 and the history button 326 of FIG. 11 function in exactly the same way as the start/stop and history buttons 46 and 48 described above in conjunction with the embodiment of the timer assembly 14 in FIG. 1. Thus, the detachable timer assembly 314 illustrated in FIG. 11 is also labeled a "2 button" embodiment.

It should be appreciated that the detachable timer assembly 314 could also be comprised of an embodiment having a "3 button" arrangement, similar to that disclosed and discussed above in connection with FIG. 6. In a "3 button" embodiment, the first actuating means in FIG. 11 would be comprised of a "inflate" button and a "deflate" button, both of which would function in a manner identical to that discussed above in connection with the inflate and deflate buttons 245, 247 of FIG. 6.

In the 2 or 3 button embodiments, the detachable timer assembly 314 is further comprised of a memory means for storing the duration of each event of inflation and deflation. In this manner, the historical timing information can be electronically stored and later recalled by actuating the buttons in the, previously described manner. In a preferred embodiment, the memory means will be comprised of a conventional random access memory arrangement (not shown), but could also be comprised of a variety of equivalent electrical components that are well known in the art.

The detachable timer assembly 314 could also be comprised of a single button embodiment, wherein the detachable timer assembly would only show the duration of the current inflation event, and the duration of the immediately past event. In such an embodiment, the first actuating means would be comprised of a single button, and there would not be a second actuating means. The single button would then function in a manner similar to that described in conjunction with FIG. 10 above.

As with the timer assembly discussed above, the detachable timer assembly 314 is battery powered (not shown). The detachable timer assembly 314 is also activated by using an on/off switch (not shown), which is preferably located on the side of the assembly 314. Activation of the on/off switch results in the same operational sequence described above in connection with the timer assembly 14.

With continued reference to FIG. 11, it is shown that an attachment means is affixed to the syringe assembly 310. The attachment means, as for example a housing 316, is for detachably receiving and mounting the detachable timer assembly 314 to the syringe assembly 310. Preferably, the housing 316 is formed as an integral part of the syringe assembly 310 and is constructed of a polycarbonate, medical grade plastic material.

Figure 12:
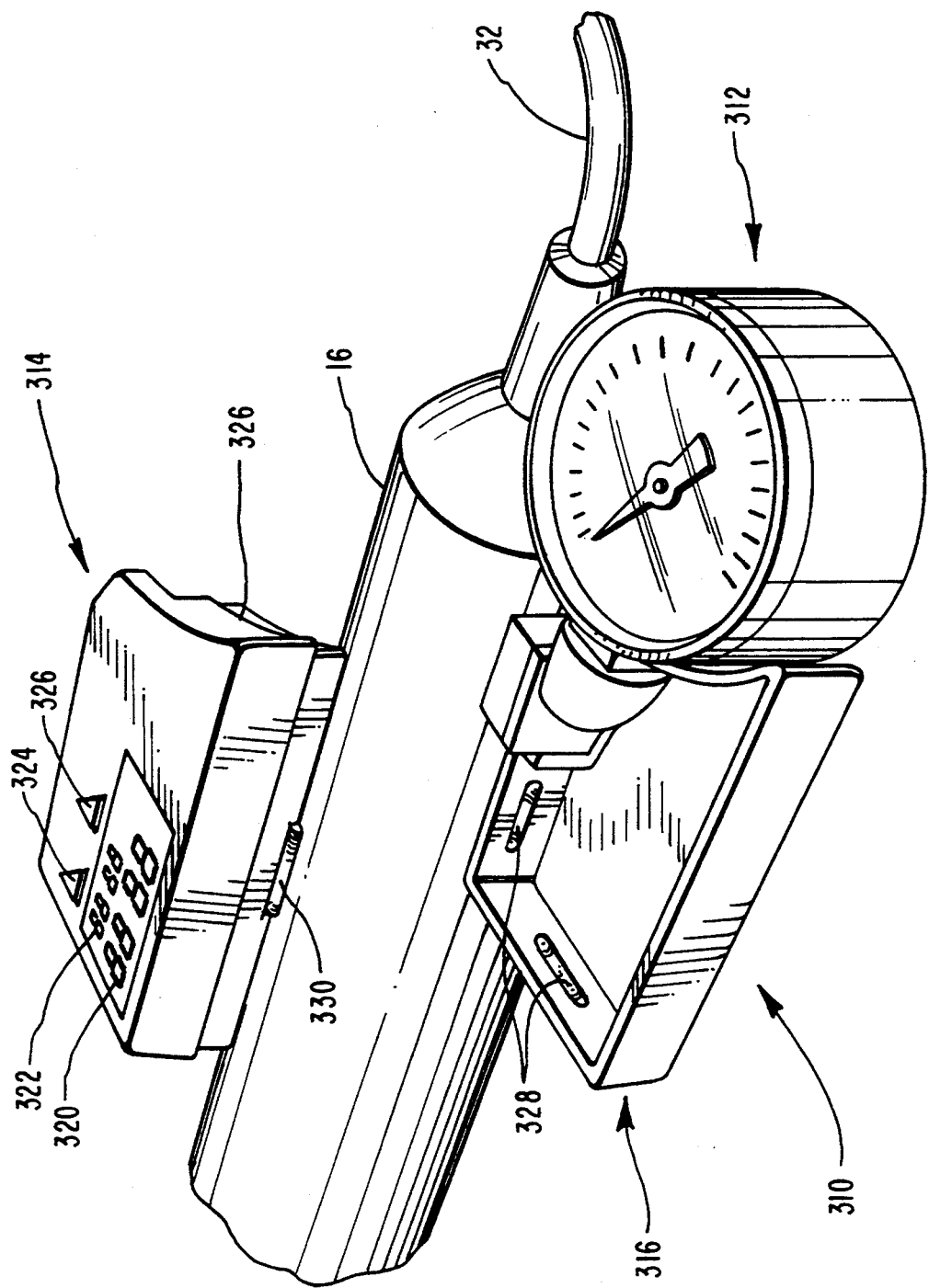
FIG. 12 is a partial perspective view of the detachable timer of FIG. 11 being detached from the syringe, and the housing disposed on the syringe which receives the detachable timer.

FIG. 12 illustrates the detachable timer assembly 314 and the housing 316 in more detail. There, the detachable timer assembly 314 is shown in a detached state. The detachable timer 314 is preferably comprised of a single module 326 that is constructed with a polycarbonate, medical grade plastic material. Also shown is the attachment means, or housing 316, which is permanently affixed to the syringe barrel 16, and preferably is formed as an integral part of the syringe barrel 16. As is shown, the housing 316 is geometrically shaped and sized so as to be capable of receiving the module 326 containing the detachable timer 314 in a tight fitting, yet releasable manner. As is further illustrated, the housing 316 is placed immediately adjacent to the pressure gauge 312 so that the operator can easily observe both the detachable timer 314 and the pressure gauge 312 while operating the syringe.

Preferably, and as is illustrated in FIG. 12, the housing 316 is further comprised of a retaining means for holding and maintaining the detachable timer assembly 314 within the housing 316. In FIG. 12, the retaining means is shown as being comprised of, for example, a plurality of receiving slots 328 that are formed as concave recesses on the interior walls of the housing 316. The receiving slots 328 correspond in size and in shape to an equal number of fastening ridges 330 that are formed on the exterior walls of the module 326 enclosing the detachable timer assembly 314. When the module 326 is received within the housing 316, the fastening ridges 330 are received in a tight snap-fit manner within the receiving slots 328. In this manner, the module 326 is tightly held within the housing 316, and will remain so until the user applies a pulling force on the module 326 so as to disengage the fastening ridges 330 from the receiving slots 328 and thereby release the module 326 from the housing 316. It should be appreciated that the function provided by the retaining means can be provided by a number of equivalent structures, including, but not limited to, a hook and fastener attachment, a threaded attachment via a hand operable bolt, a hand operable clamp or clasp attachment, and even a releasable adhesive attachment, such as with a Velcro ® fastener.

As is further shown in FIG. 12, the pressure gauge 312 is permanently affixed to the syringe barrel 16. In this embodiment, tile pressure gauge 312 is in direct fluid communication with the interior of the syringe barrel 16 through a port (not shown) in a manner essentially identical to that discussed in relation to FIG. 2 above.

In operation, the detachable timer assembly 314 functions exactly the same as the timer assembly 14 discussed above in connection with FIG. 1. The discussion pertaining to the various display conditions illustrated in FIGS. 3 and 4 also apply to the detachable timer assembly 314. Similarly, the flow chart of the 2 button timer illustrated in FIGS. 5A, 5B and 5C sets forth the preferred flow of operations for the 2 button version of the detachable timer assembly 314. Finally, if the detachable timer assembly 314 is configured as a 1 or 3 button timer, then the discussions in connection with those particular versions also apply.

Figure 13:
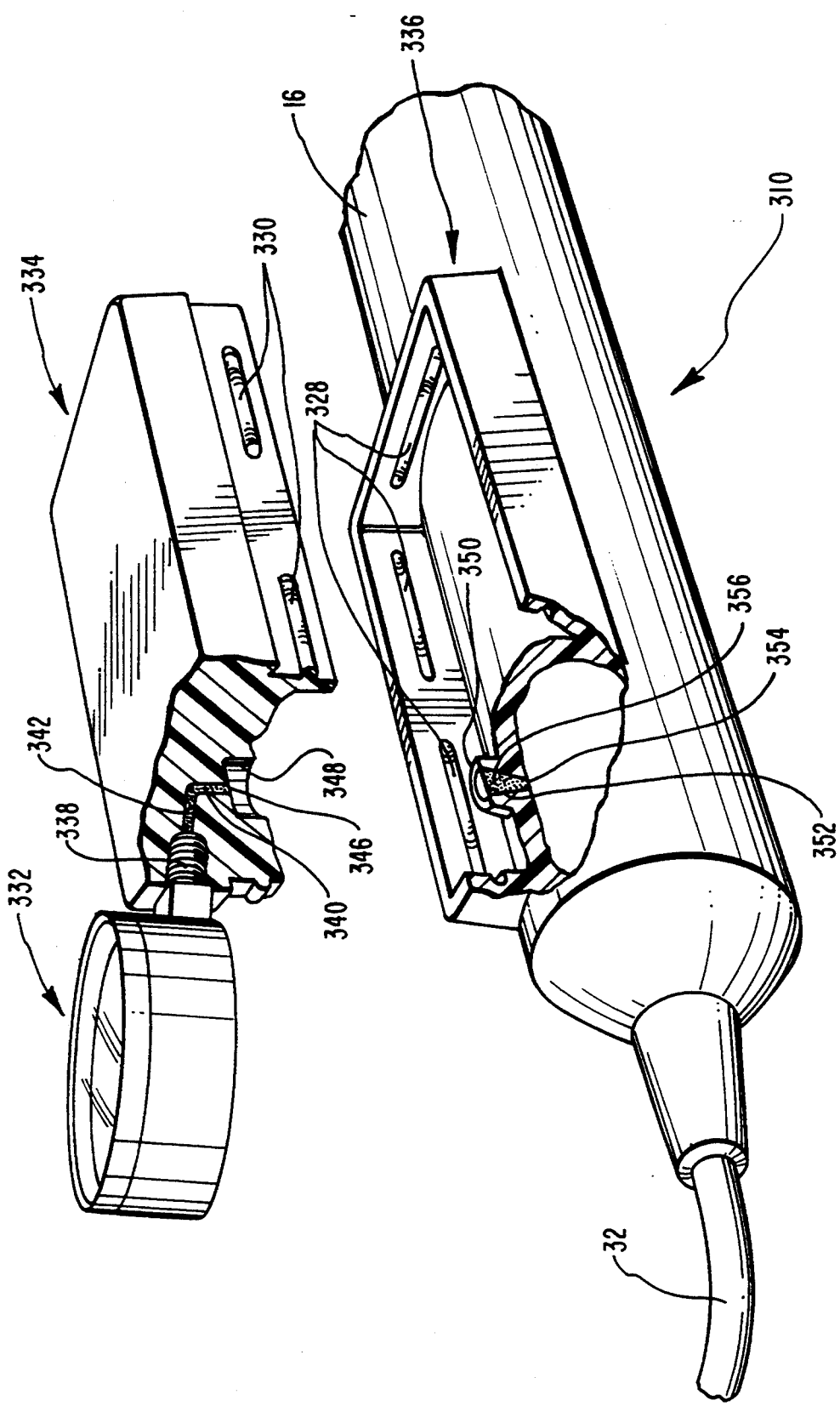
FIG. 13 is a partial perspective view of another embodiment of the detachable timer wherein the pressure gauge is mounted to the timer.

Referring now to FIG. 13, another presently preferred embodiment of the syringe apparatus 310 is shown. In this particular embodiment, rather than being permanently mounted to the syringe barrel 16, the pressure gauge means, as for example a conventional strain pressure gauge 332, is mounted to the detachable timer means, as for example the detachable timer assembly 334 shown in FIG. 13. In this manner, the pressure gauge 332 is detachable along with the detachable timer assembly 334 and is therefore also reusable. This additional capability further reduces the overall cost of each angioplasty procedure.

As is illustrated in FIG. 13, the pressure gauge 332 is mounted to the detachable timer assembly 334 via a threaded, or similar engagement, shown at 338. The pressure gauge 332 is then placed in fluid communication with the interior of the syringe barrel 16 when the detachable timer assembly 334 is detachably mounted to the syringe assembly via the attachment means, or housing 336.

FIG. 13 further illustrates one preferred manner in which the fluid communication between the pressure gauge means and the contents of the syringe barrel is accomplished. Pressure gauge 332, when mounted to the detachable timer assembly 334, is coupled to a fluid pressure transmitting medium, as for example a first silicone gel filled diaphragm 340. This gel filled diaphragm 340 is disposed entirely within an elongate cylindrical bore 342 that extends out through an opening 346. The opening 346 exits the module 344 at a point that is centrally disposed within a cylindrically shaped recessed area 348 that is formed in the bottom of the module 344.

As is further illustrated in FIG. 13, formed on the syringe barrel 16 at a point within the housing is a cylindrically shaped port 350. The exterior of port 350 is geometrically shaped so as to be capable of being tightly received within the recessed area 348. Formed within the port 350 is a conically shaped bore 352 which extends through the wall of the syringe barrel 16 thereby forming a small circular opening 354. Disposed within the conically shaped bore 352 is a fluid pressure transmitting medium, as for example a second silicone gel filled diaphragm 356.

Figure 14:
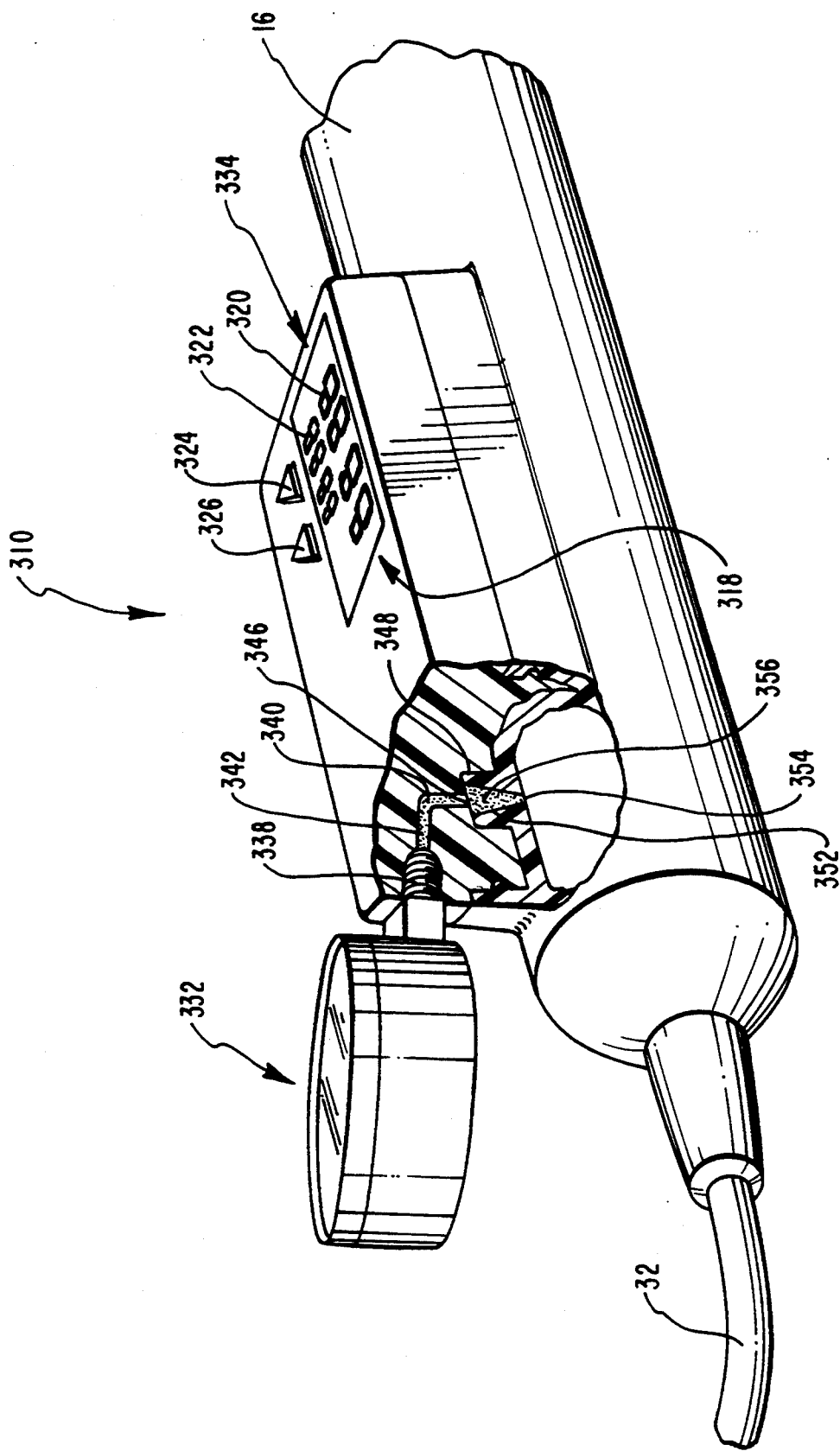
FIG. 14 is a partial perspective view of the detachable timer of FIG. 13 being detachably mounted to the syringe.

When the detachable timer assembly 334 is detachably mounted to the housing 336, as is shown in FIG. 14, the recessed area 348 receives the port 350 in a manner such that the first gel filled diaphragm 340 is placed in direct contact with the second gel filled diaphragm 356. The pressure gauge 332 is thus in indirect fluid communication with the contents of the syringe barrel 16. Consequently, fluid pressures exerted within the syringe barrel 16 and the pressure tubing 32 are transmitted to the pressure gauge 332 so that such fluid pressures can be sensed and displayed by the pressure gauge 332.

The detachable timer assembly 334 in FIGS. 13 and 14 is otherwise identical in all other respects to the detachable timer assembly 314 of FIGS. 11 and 12, and it may also be configured as a one, two or three button timer.

A presently preferred construction of a detachable timer assembly disclosed in FIGS. 11–14 is essentially the same as that illustrated in FIG. 7 and discussed above. Thus, the detachable timer assembly is preferably comprised of a liquid crystal display, a diffuser and an electronic timer module which includes the electronic components of the detachable timer assembly and the battery to operate them. It will be appreciated that the primary difference is that the components are housed in a detachable module 326, rather than being permanently mounted to the syringe barrel, as in FIG. 7. Preferably, the module 326 is hermetically sealed. In this way, the components that make up the detachable timer are protected from the various liquids and/or temperatures that are present in the various sterilization techniques that may be used to sterilize the detachable timer assembly.

It will be appreciated that the present invention may be embodied in other specific forms without departing from its spirit or essential characteristics. The described embodiments are to be considered in all respects only as illustrative and not restrictive, and the scope of the invention is indicated by the appended claims rather than by the foregoing description. All changes which come within the meaning and range of equivalency of the claims are to be embraced within their scope.

What is claimed and desired to be secured by United States Patent is:

1. An apparatus for use in inflating a balloon-tipped catheter, comprising:
   syringe means for generating sufficient pressure to inflate a balloon-tipped catheter;
   pressure gauge means, attached to the syringe means, for measuring and displaying the pressure generated by the syringe means;
   detachable and reusable timer means, removably attached to the syringe means as an integral part thereof, for measuring durations of separate events of inflation and deflation of the balloon-tipped catheter, said detachable and reusable timer means including:
      display means for visually displaying the time durations measured by the detachable and reusable timer means since commencement of a current event of inflation and deflation, as applicable and wherein the display means further includes a display simultaneously showing the duration of the immediate past event of inflation and deflation, as applicable; and
      first actuating means for commencing the timing of the duration of each successive event of inflation and deflation; and
   attachment means on the syringe means for detachably receiving said detachable and reusable timer means as an integral part of the syringe means, and whereby the detachable and reusable timer means is also detachable from the syringe means for re-use with another syringe means.

2. An apparatus as defined in claim 1 wherein said detachable and reuseable timer means further comprises:
   memory means for storing the duration of each event of inflation and deflation; and
   second actuating means for causing the display means to display the historical duration of each event of inflation and deflation stored in the memory means.

3. An apparatus as defined in claim 1, wherein the display means comprises a liquid crystal display that is mounted and electrically connected to the detachable timer means.

4. An apparatus as defined in claim 1, wherein the pressure gauge means is mounted to said syringe means.

5. An apparatus as defined in claim 1, wherein the pressure gauge means is mounted to said detachable and reusable timer means, such that the pressure gauge means is detachable from the syringe means together with the detachable and reusable timer means.

6. An apparatus as defined in claim 1, wherein said attachment means comprises:
   a housing, said housing being affixed to said syringe means and being sized and shaped so as to receive and detachably hold said detachable and reusable timer means.

7. An apparatus as defined in claim 6, wherein said housing comprises:
   retaining means for maintaining said detachable and reusable timer means within said housing in a tight, yet releasable manner.

8. An apparatus for use in inflating a balloon-tipped catheter, comprising:
   syringe means for generating sufficient pressure to inflate a balloon-tipped catheter;
   pressure gauge means, mounted to said syringe means, for measuring and displaying the pressure generated by the syringe means;
   detachable and reusable timer means, detachably mountable to said syringe means, for measuring durations of separate events of inflation and deflation of the balloon-tipped catheter, said detachable and reusable timer means including:
      display means for visually displaying the time durations measured by the detachable and reusable timer means;
      first actuating means for commencing the timing of the duration of each successive event of inflation and deflation;
      memory means for storing the duration of each event of inflation and deflation; and
      second actuating means for causing the display means to display the historical duration of each event of inflation and deflation stored in the memory means; and
   attachment means, affixed to said syringe means, for detachably mounting said detachable and reusable timer means to the syringe means, whereby the detachable and reusable timer means is detachable from the syringe means so as to be reusable with another syringe means.

9. An apparatus as defined in claim 8, wherein said attachment means comprises:
   a housing, said housing being affixed to said syringe means and being sized and shaped so as to receive and detachably hold said detachable timer means.

10. An apparatus as defined in claim 9, wherein said housing comprises:

retaining means for maintaining said detachable timer means within said housing in a tight yet releasable manner.

11. An apparatus as defined in claim 8, wherein the display means comprises a liquid crystal display that is mounted and electrically connected to the detachable timer means.

12. An apparatus for use in inflating a balloon-tipped catheter, comprising:
  syringe means for generating sufficient pressure to inflate a balloon-tipped catheter;
  pressure gauge means, attached to the syringe means, for measuring and displaying the pressure generated by the syringe means;
  detachable and reusable timer means, detachably mountable to said syringe means, for measuring durations of separate events of inflation and deflation of the balloon-tipped catheter, said detachable and reusable timer means having said pressure gauge means mounted thereto and said detachable and reusable timer means further including:
    display means for visually displaying the time durations measured by the detachable and reusable timer means;
    first actuating means for commencing the timing of the duration of each successive event of inflation and deflation;
    memory means for storing the duration of each event of inflation and deflation; and
    second actuating means for causing the display means to display the historical duration of each event of inflation and deflation stored in the memory means; and
  attachment means for detachably receiving said detachable and reusable timer means, whereby the pressure gauge means is detachable from the syringe means along with the detachable and reusable timer means so as to be reusable with another syringe means.

13. An apparatus as defined in claim 12, wherein said attachment means comprises:
  a housing, said housing being affixed to said syringe means and being sized and shaped so as to receive and detachably hold said detachable and reusable timer means.

14. An apparatus as defined in claim 13 wherein said housing comprises:
  retaining means for maintaining said detachable and reusable timer means within said housing in a tight yet releasable manner.

15. An apparatus as defined in claim 12, wherein the display means comprises a liquid crystal display that is mounted and electrically connected to the detachable and reusable timer means.

16. An apparatus for use in inflating a balloon-tipped catheter, comprising:
  (a) syringe means for generating sufficient pressure to inflate a balloon-tipped catheter;
  (b) pressure gauge means, mounted to said syringe means, for measuring and displaying the pressure generated by the syringe means;
  (c) detachable and reusable timer means, detachably mountable to said syringe means, for measuring durations of separate events of inflation and deflation of the balloon-tipped catheter, said detachable and reusable timer means including:
    (i) display means for visually displaying the time durations measured by the detachable timer means;
    (ii) first actuating means for commencing the timing of the duration of each successive, event of inflation and deflation;
    (iii) memory means for storing the duration of each event of inflation and deflation; and
    (iv) second actuating means for causing the display means to display the historical duration of each event of inflation and deflation stored in the memory means; and
  (d) attachment means, affixed to said syringe means, for detachably mounting said detachable and reusable timer means to the syringe means, whereby the detachable timer means is detachable from the syringe means so as to be reusable in another syringe means, the attachment means comprising:
    (i) a housing, said housing being affixed to said syringe means and being sized and shaped so as to receive and detachably hold said detachable timer means; and
    (ii) retaining means for maintaining said detachable and reusable timer means within said housing in a tight yet releasable manner.

17. An apparatus for use in inflating a balloon-tipped catheter, comprising:
  (a) syringe means for generating sufficient pressure to inflate a balloon-tipped catheter;
  (b) pressure gauge means for measuring and displaying the pressure generated by the syringe means;
  (c) detachable and reusable timer means, detachably mountable to said syringe means, for measuring durations of separate events of inflation and deflation of the balloon-tipped catheter, said detachable and reusable timer means having said pressure gauge means mounted thereto and said detachable timer means further including:
    (i) display means for visually displaying the time durations measured by the detachable and reusable timer means;
    (ii) first actuating means for commencing the timing of the duration of each successive event of inflation and deflation;
    (iii) memory means for storing the duration of each event of inflation and deflation; and
    (iv) second actuating means for causing the display means to display the historical duration of each event of inflation and deflation stored in the memory means; and
  (d) attachment means, affixed to said syringe means, for detachably mounting said detachable and reusable timer means to the syringe means, whereby the pressure gauge means is detachable from the syringe means along with the detachable and reusable timer means, so as to be reusable on another syringe means, the attachment means comprising:
    (i) a housing, said housing being affixed to said syringe, means and being sized and shaped so as to receive and detachably hold said detachable timer means; and
    (ii) retaining means for maintaining said detachable timer means within said housing in a tight yet releasable manner.

* * * * *

UNITED STATES PATENT AND TRADEMARK OFFICE
CERTIFICATE OF CORRECTION

PATENT NO. : 5,449,344
DATED : September 12, 1995
INVENTOR(S) : STEVEN R. TAYLOR et al.

It is certified that error appears in the above-indentified patent and that said Letters Patent is hereby corrected as shown below:

Title page, page 2, column 2, line 11 of "Other Publications," after "Pump" insert --(1988)--

Page 3 of patent, column 1, last line after "WO92/17221  10/1992 WIPO," insert  --0446932A2  3/91  EPO--

Page 3 of patent, column 2, second to last line, "filling date" should be --filing date--

Column 4, line 13, "is partial" should be --is a partial--

Column 8, line 66, "48 history button" should be --history button 48--

Column 9, lines 39-40, "delation event" should be --deflation event--

Column 12, line 50, "a "inflate" button" should be --an "inflate" button--

Column 12, line 59, "the," should be --the--

Column 18, line 61, "syringe, means" should be --syringe means-- .

Signed and Sealed this

Twentieth Day of August, 1996

Attest:

BRUCE LEHMAN

Attesting Officer
Commissioner of Patents and Trademarks